United States Patent
Ali et al.

(10) Patent No.: US 6,684,090 B2
(45) Date of Patent: Jan. 27, 2004

(54) PULSE OXIMETRY DATA CONFIDENCE INDICATOR

(75) Inventors: Ammar Al Ali, Tustin, CA (US); Divya S. Breed, Laguna Niguel, CA (US); Jerome J. Novak, Aliso Viejo, CA (US); Massi E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 36 days.

(21) Appl. No.: 09/858,114

(22) Filed: May 15, 2001

(65) Prior Publication Data

US 2002/0035315 A1 Mar. 21, 2002

Related U.S. Application Data

(63) Continuation-in-part of application No. 09/478,230, filed on Jan. 6, 2000.
(60) Provisional application No. 60/115,289, filed on Jan. 7, 1999.

(51) Int. Cl.[7] ................................................. A61B 5/00
(52) U.S. Cl. ...................... 600/323; 600/324; 600/336
(58) Field of Search ................................. 600/309–310, 600/322–324, 330, 331, 336

(56) References Cited

U.S. PATENT DOCUMENTS

| | | |
|---|---|---|
| 3,875,930 A | 4/1975 | Silva et al. |
| 4,193,393 A | 3/1980 | Schlager |

(List continued on next page.)

FOREIGN PATENT DOCUMENTS

| | | |
|---|---|---|
| DE | 3723566 | 1/1989 |

(List continued on next page.)

OTHER PUBLICATIONS

Michael W. Wukitsch et al., "Pulse Oximetry: Analysis of Theory, Technology, and Practice," Journal of Clinical Monitoring, vol. 4, No. 4, pp. 290–301 (Oct. 1998).

*Primary Examiner*—Eric F. Winakur
*Assistant Examiner*—Matthew Kremer
(74) *Attorney, Agent, or Firm*—Knobbe, Martens, Olson & Bear, LLP

(57) ABSTRACT

An intelligent, rule-based processor provides a pulse indicator designating the occurrence of each pulse in a pulse oximeter-derived photo-plethysmograph waveform. When there is relatively no distortion corrupting the plethysmograph signal, the processor analyzes the shape of the pulses in the waveform to determine where in the waveform to generate the pulse indication. When distortion is present, looser waveform criteria are used to determine if pulses are present. If pulses are present, the pulse indication is based upon an averaged pulse rate. If no pulses are present, no indication occurs. The pulse indicator provides a trigger and amplitude output. The trigger output is used to initiate an audible tone "beep" or a visual pulse indication on a display, such as a vertical spike on a horizontal trace or a corresponding indication on a bar display. The amplitude output is used to indicate data integrity and corresponding confidence in the computed values of saturation and pulse rate. The amplitude output can vary a characteristic of the pulse indicator, such as beep volume or frequency or the height of the visual display spike.

The visual pulse indicator is supplemented by a signal quality alert. Combined with several indicators of signal quality, the alert is used to initiate a warning when data confidence is very low. The alert may be in the form of a message generated on the pulse oximeter display to warn that the accuracy of saturation and pulse rate measurements may be compromised. A confidence-based alarm utilizes signal quality measures to reduce the probability of false alarms when data confidence is low and to reduce the probability of missed events when data confidence is high.

15 Claims, 24 Drawing Sheets

U.S. PATENT DOCUMENTS

| | | |
|---|---|---|
| 4,222,044 A | 9/1980 | Boschung |
| 4,694,200 A | 9/1987 | Hetyei |
| 4,863,265 A * | 9/1989 | Flower et al. ................. 356/41 |
| 5,199,048 A | 3/1993 | Wakabayashi |
| 5,372,134 A | 12/1994 | Richardson |
| 5,517,988 A | 5/1996 | Gerhard |
| 5,751,911 A | 5/1998 | Goldman |
| 5,810,740 A * | 9/1998 | Paisner ....................... 600/515 |
| 5,819,007 A | 10/1998 | Elghazzawi |
| 5,865,736 A | 2/1999 | Baker, Jr. et al. |
| 6,002,952 A | 12/1999 | Diab et al. |
| 6,047,201 A * | 4/2000 | Jackson, III ................ 600/344 |
| 6,339,715 B1 | 1/2002 | Bahr et al. |
| 6,358,213 B1 * | 3/2002 | Friedman et al. ........... 600/493 |
| 6,415,166 B1 * | 7/2002 | Van Hoy et al. ............ 600/323 |

FOREIGN PATENT DOCUMENTS

| | | |
|---|---|---|
| EP | 617912 | 10/1994 |
| EP | 813102 | 5/1997 |
| WO | WO 98/43071 | 10/1998 |
| WO | WO 00/38569 | 7/2000 |
| WO | WO 00/40147 | 7/2000 |
| WO | WO 00/56209 | 9/2000 |
| WO | WO 00/61000 | 10/2000 |

* cited by examiner

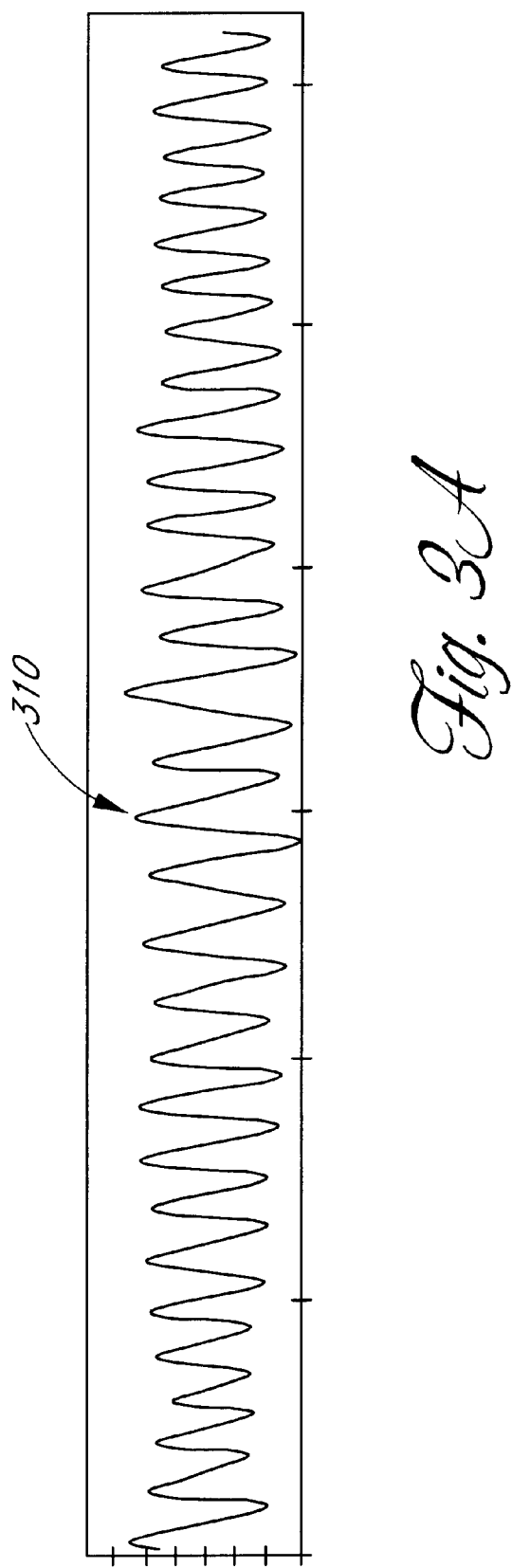

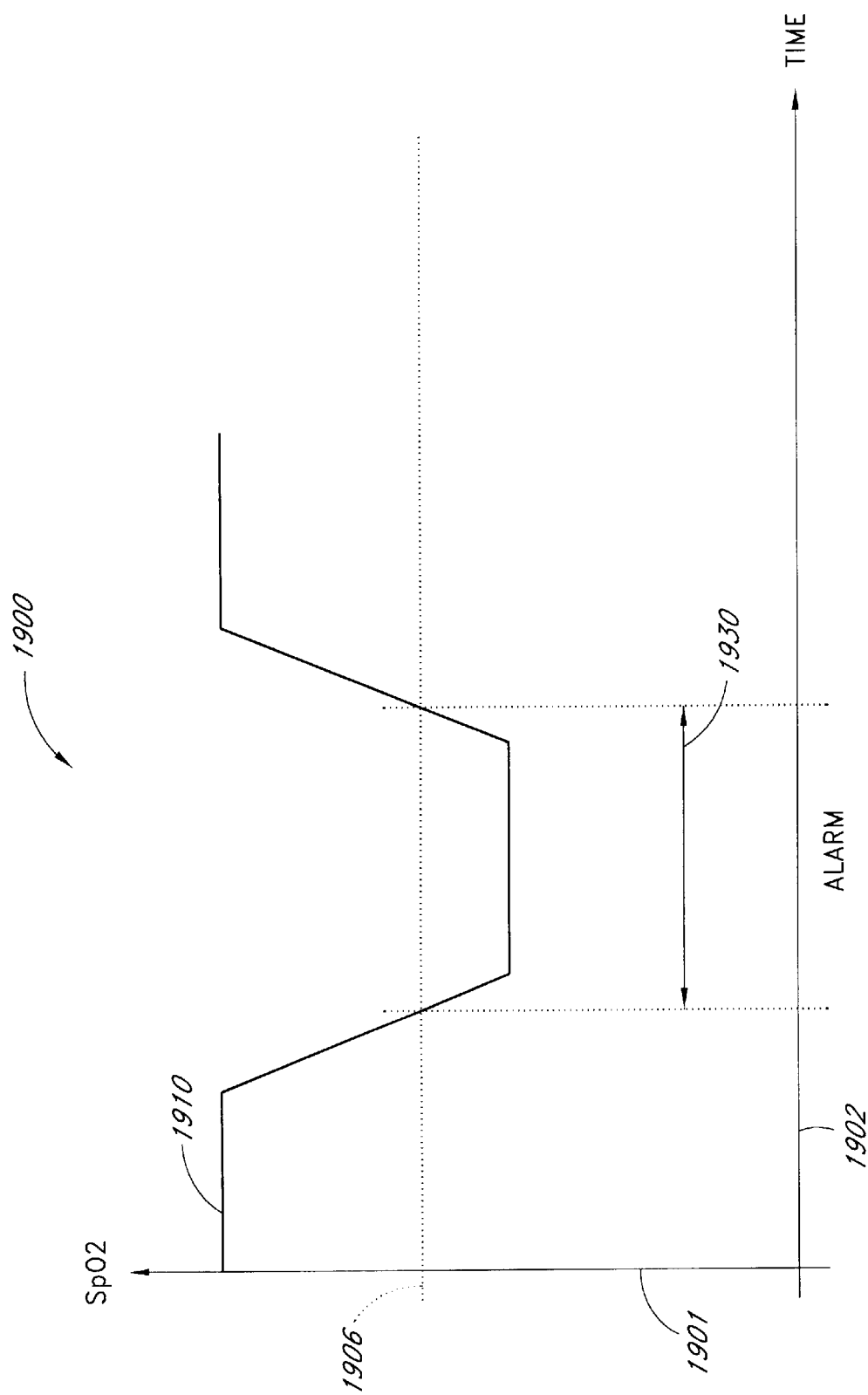

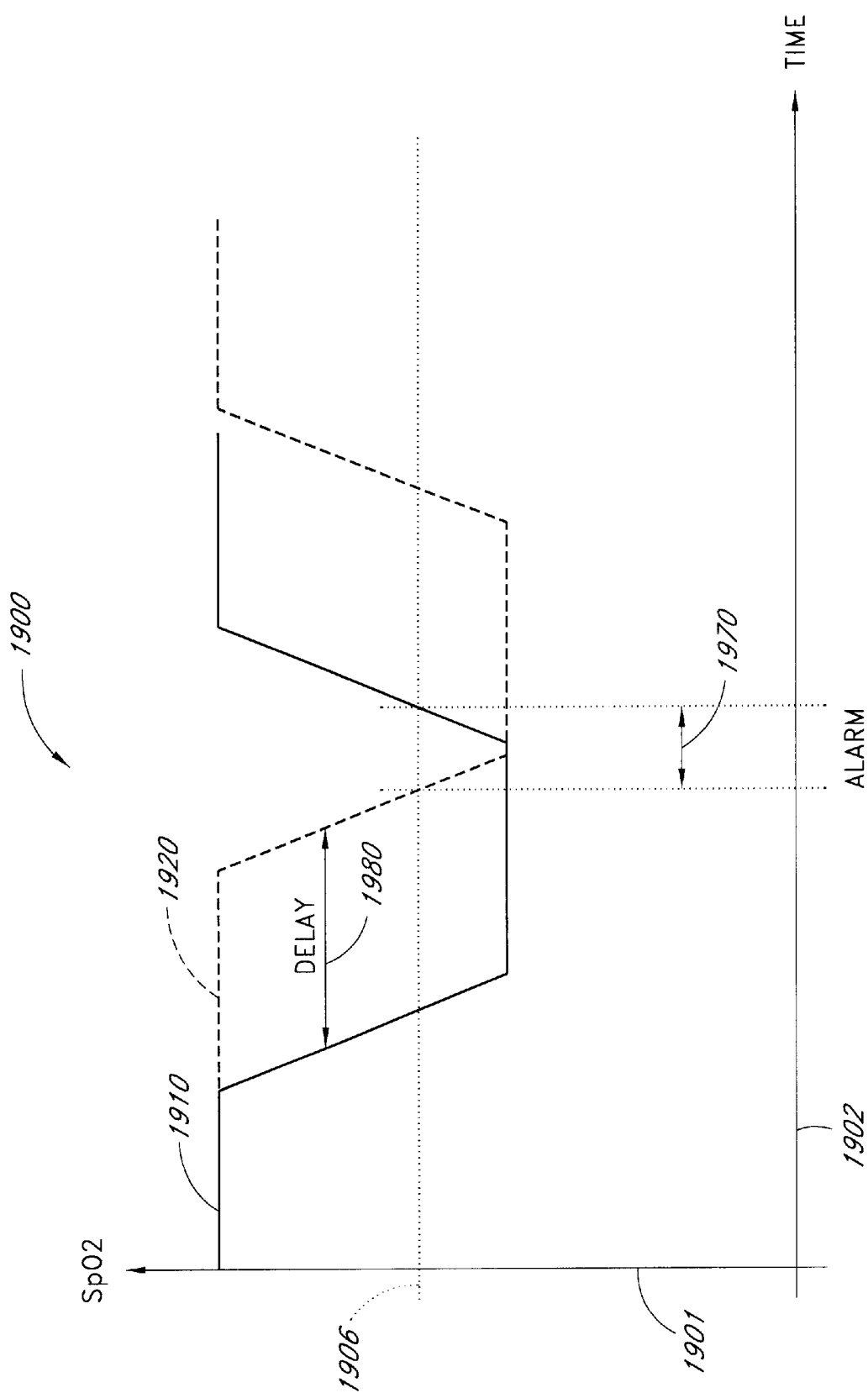

PULSE OXIMETRY DATA CONFIDENCE INDICATOR

This is a continuation-in-part of U.S. patent application Ser. No. 09/478,230 entitled "Pulse Oximetry Pulse Indicator," filed Jan. 6, 2000, which relates to and claims the benefit of prior provisional application 60/115,289, filed Jan. 7, 1999.

BACKGROUND OF THE INVENTION

Oximetry is the measurement of the oxygen status of blood. Early detection of low blood oxygen is critical in the medical field, for example in critical care and surgical applications, because an insufficient supply of oxygen can result in brain damage and death in a matter of minutes. Pulse oximetry is a widely accepted noninvasive procedure for measuring the oxygen saturation level of arterial blood, an indicator of oxygen supply. A pulse oximeter typically provides a numerical readout of the patient's oxygen saturation, a numerical readout of pulse rate, and an audible indicator or "beep" that occurs in response to each pulse. In addition, a pulse oximeter may display the patient's plethysmograph waveform, which is a visualization of blood volume change in the illuminated tissue caused by pulsatile arterial blood flow over time. The plethysmograph provides a visual display that is also indicative of the patient's pulse and pulse rate.

A pulse oximetry system consists of a sensor attached to a patient, a monitor, and a cable connecting the sensor and monitor. Conventionally, a pulse oximetry sensor has both red and infrared (IR) light-emitting diode (LED) emitters and a photodiode detector. The sensor is typically attached to a patient's finger or toe, or a very young patient's patient's foot. For a finger, the sensor is configured so that the emitters project light through the fingernail and into the blood vessels and capillaries underneath. The photodiode is positioned at the fingertip opposite the fingernail so as to detect the LED transmitted light as it emerges from the finger tissues.

The pulse oximetry monitor (pulse oximeter) determines oxygen saturation by computing the differential absorption by arterial blood of the two wavelengths emitted by the sensor. The pulse oximeter alternately activates the sensor LED emitters and reads the resulting current generated by the photodiode detector. This current is proportional to the intensity of the detected light. The pulse oximeter calculates a ratio of detected red and infrared intensities, and an arterial oxygen saturation value is empirically determined based on the ratio obtained. The pulse oximeter contains circuitry for controlling the sensor, processing the sensor signals and displaying the patient's oxygen saturation and pulse rate. A pulse oximeter is described in U.S. Pat. No. 5,632,272 assigned to the assignee of the present invention.

SUMMARY OF THE INVENTION

FIG. 1 illustrates the standard plethysmograph waveform 100, which can be derived from a pulse oximeter. The waveform 100 is a display of blood volume, shown along the y-axis 110, over time, shown along the x-axis 120. The shape of the plethysmograph waveform 100 is a function of physiological conditions including heart stroke volume, pressure gradient, arterial elasticity and peripheral resistance. The ideal waveform 100 displays a broad peripheral flow curve, with a short, steep inflow phase 130 followed by a 3 to 4 times longer outflow phase 140. The inflow phase 130 is the result of tissue distention by the rapid blood volume inflow during ventricular systole. During the outflow phase 140, blood flow continues into the vascular bed during diastole. The end diastolic baseline 150 indicates the minimum basal tissue perfusion. During the outflow phase 140 is a dicrotic notch 160, the nature of which is disputed. Classically, the dicrotic notch 160 is attributed to closure of the aortic valve at the end of ventricular systole. However, it may also be the result of reflection from the periphery of an initial, fast propagating, pressure pulse that occurs upon the opening of the aortic valve and that precedes the arterial flow wave. A double dicrotic notch can sometimes be observed, although its explanation is obscure, possibly the result of reflections reaching the sensor at different times.

FIGS. 2–4 illustrate plethysmograph waveforms 200, 310, 360 that display various anomalies. In FIG. 2, the waveform 200 displays two arrhythmias 210, 220. In FIG. 3, the waveform 310 illustrates distortion corrupting a conventional plethysmograph 100 (FIG. 1). FIG. 4 shows a filtered waveform 360 after distortion has been removed through adaptive filtering, such as described in U.S. Pat. No. 5,632, 272 cited above. FIG. 4 illustrates that, although the waveform 360 is filtered, the resulting pulses 362 have shapes that are distorted in comparison to the pulses illustrated in FIG. 1.

A desirable feature of pulse oximeters is an audible "beep" tone produced to correspond to the patient's pulse. Conventionally, the beep is triggered from recognition of some aspect of the plethysmograph waveform shape. Such a waveform-triggered beep may indicate an arrhythmia, like those displayed in FIG. 2, but may also generate false pulse indications as the result of motion-artifact or noise induced waveform distortion, as illustrated in FIGS. 3 and 4. This characteristic results because both distortion and arrhythmias result in anomalies in the plethysmograph waveform shape on which this beep mechanism is dependent. Alternatively, the beep can be triggered from a time base set to the average pulse rate. Signal processing can generate an average pulse rate that is resistant to distortion induced error. A pulse beep based on average pulse rate is relatively insensitive to episodes of distortion, but is likewise insensitive to arrhythmias.

An example of the determination of pulse rate in the presence of distortion is described in U.S. Pat. No. 6,002, 952, filed Apr. 14, 1997, entitled "Signal Processing Apparatus and Method," which is assigned to the assignee of the current application and incorporated by reference herein. Another example of pulse rate determination in the presence of distortion is described in U.S. patent application Ser. No. 09/471,510, filed Dec. 23, 1999, entitled "Plethysmograph Pulse Recognition Processor," which is assigned to the assignee of the current application and incorporated by reference herein.

One aspect of the present invention is a processor having a decision element that determines if the waveform has little or no distortion or significant distortion. If there is little distortion, the decision element provides a trigger in real-time with physiologically acceptable pulses recognized by a waveform analyzer. If there is significant distortion, then the decision element provides the trigger based synchronized to an averaged pulse rate, provided waveform pulses are detected. The trigger can be used to generate an audible pulse beep that is insensitive to episodes of significant distortion, but is capable of responding to arrhythmia events.

Another desirable feature for pulse oximeters is a visual indication of the patient's pulse. Conventionally, this is provided by an amplitude-versus-time display of the plethysmograph waveform, such as illustrated in FIG. 1.

Some monitors are only capable of a light-bar display of the plethysmograph amplitude. Regardless, both types of displays provide a sufficient indication of the patient's pulse only when there is relatively small distortion of the plethysmograph waveform. When there is significant distortion, such as illustrated in FIG. 3A, the display provides practically no information regarding the patient's pulse.

Yet another desirable feature for pulse oximeters is an indication of confidence in the input data. Conventionally, a visual display of a plethysmograph waveform that shows relatively small distortion would convey a high confidence level in the input data and a corresponding high confidence in the saturation and pulse rate outputs of the pulse oximeter. However, a distorted waveform does not necessarily indicate low confidence in the input data and resulting saturation and pulse rate outputs, especially if the pulse oximeter is designed to function in the presence of motion-artifact.

Another aspect of the current invention is the generation of a data integrity indicator that is used in conjunction with the decision element trigger referenced above to create a visual pulse indicator. The visual pulse indicator is an amplitude-versus-time display that can be provided in conjunction with the plethysmograph waveform display. The trigger is used to generate a amplitude spike synchronous to a plethysmograph pulse. The data integrity indicator varies the amplitude of the spike in proportion to confidence in the measured values.

Yet another aspect of the present invention is a processing apparatus that has as an input a plethysmograph waveform containing a plurality of pulses. The processor generates a trigger synchronous with the occurrence of the pulses. The processor includes a waveform analyzer having the waveform as an input and responsive to the shape of the pulses. The processor also includes a decision element responsive to the waveform analyzer output when the waveform is substantially undistorted and responsive to pulse rate when the waveform is substantially distorted. The trigger can be used to generate an audible or visual indicator of pulse occurrence. A measure of data integrity can also be used to vary the audible or visual indicators to provide a simultaneous indication of confidence in measured values, such as oxygen saturation and pulse rate.

A further aspect of the current invention is a method of indicating a pulse in a plethysmograph waveform. The method includes the steps of deriving a measure of distortion in the waveform, establishing a trigger criterion dependent on that measure, determining whether the trigger criterion is satisfied to provide a trigger, and generating a pulse indication upon occurrence of the trigger. The deriving step includes the substeps of computing a first value related to the waveform integrity, computing a second value related to the recognizable pulses in the waveform, and combining the first and second values to derive the distortion measure. The trigger criterion is based on waveform shape and possibly on an averaged pulse rate.

One more aspect of the current invention is an apparatus for indicating the occurrence of pulses in a plethysmograph waveform. This apparatus includes a waveform analyzer means for recognizing a physiological pulse in the waveform. Also included is a detector means for determining a measure of distortion in the waveform and a decision means for triggering an audible or visual pulse indicator. The decision means is based the physiological pulse and possibly the pulse rate, depending on the distortion measure.

Another aspect of the present invention is a data confidence indicator comprising a plurality of physiological data and a plurality of signal quality measures derived from a physiological sensor output. A plurality of comparator outputs are each responsive to one of the measures and a corresponding one of a plurality of thresholds. An alert trigger output combines said comparator outputs, and a low signal quality warning is generated in response to said alert trigger output. The thresholds are set so that the warning occurs during a time period when there is low confidence in the data. In one embodiment, the warning is a display message that supplements a visual pulse indicator, the display message specifies a low signal quality when the visual pulse indicator has an amplitude that is less than one-third full-scale. In another embodiment, the signal quality measures are an integrity measure, a pulse rate density measure and a harmonic ratio measure. In a particular embodiment, the thresholds may have an integrity value of less than 0.3, a pulse rate density value of less than 0.7 and a harmonic ratio value of less than 0.8.

In yet another embodiment a filter for the data generates a smoothed data output. An adjustment for the smoothed data output is a function of at least one of the signal quality measures so that smoothing at the smoothed data output increases when at least one of the signal quality measures decreases. An alarm trigger is responsive to the smoothed data output so as to generate an alarm when the smoothed data output is outside of a predetermined limit. In a particular embodiment the filter comprises a buffer having a buffer input and a delay output. The buffer input corresponds to the data and the delay output is time-shifted according to the adjustment. A first filter comparator output is responsive to the data and a data threshold, and a second filter comparator output is responsive to the delay output and a delay output threshold. The comparator outputs are combined so as to provide the alarm trigger.

A further aspect of the present invention is a data confidence indicator comprising a processor configured to derive a time-dependent physiological data set and a plurality of time-dependent signal quality measures from a physiological signal. A buffer is configured to time-shift the data set by a delay to generate a delayed data set, where the delay is a function of at least one of the signal quality measures. The indicator has a threshold setting a limit for the delayed data set. A warning is generated when the levels of the data set and the delayed data set are beyond that threshold. In one embodiment, a first comparator output is responsive to the data and the threshold, and a second comparator output is responsive to the delayed data set and the threshold. A combination of the first and second comparator outputs provides an alarm trigger for the warning. The data confidence indicator may also comprise a combination of the signal quality measures providing an alert trigger to generate warning when confidence in the data set is low.

An additional aspect of the present invention is a data confidence indication method comprising the steps of acquiring a signal from a physiological sensor, calculating a physiological data set from the signal, calculating signal quality measures from the signal, and indicating on a display the confidence in the data set based upon at least one of the signal quality measures. The indicating step may have the substeps of utilizing the signal quality measures to detect a low signal quality period during which time the data set may be compromised, and writing an alert message on the display during at least a portion of that period. Additional utilizing substeps may include comparing each of the signal quality measures to a corresponding one of a plurality of thresholds to generate a plurality of trigger inputs and combining the trigger inputs to trigger a low signal quality warning. Additional steps may include setting an alarm limit for the data set, filtering the data set to generate an alarm trigger based upon the alarm limit and adjusting the characteristics of the filtering step according to at least one of the signal quality measures so that more filtering is applied during the low signal quality period. In one embodiment, the filtering step comprises the substeps of time-shifting the data set to create a delayed data set, comparing the data set to a threshold to generate a first trigger input, comparing the delayed data set to the threshold to generate a second trigger input, and combining the trigger inputs to generate the alarm trigger.

Yet a further aspect of the present invention is a data confidence indication method comprising the steps of acquiring a signal from a physiological sensor, calculating a physiological data set from the signal, calculating a plurality of signal quality measures from the signal, setting an alarm threshold for the data set, and delaying an alarm trigger when the data set exceeds the threshold as a function of at least one of the signal quality measures so as to reduce the probability of false alarms. In one embodiment, the delaying step comprises the substeps of time-shifting the data set by a delay to generate a delayed data set, where the delay is a function of at least one of said signal quality measures, and comparing the data set to the threshold to create a first limit output. Further substeps include comparing the delayed data set to the threshold to create a second limit output and combining the limit outputs to generate the alarm trigger. The data confidence indication method may further comprise the steps of comparing each of the signal quality measures to a corresponding one of a plurality of thresholds to generate a plurality of trigger inputs and combining the trigger inputs to trigger a low signal quality warning.

BRIEF DESCRIPTION OF THE DRAWINGS

FIG. 3A illustrates a plethysmograph waveform corrupted by distortion;

FIGS. 19A–D are saturation versus time graphs illustrating operation of a confidence-based alarm.

DETAILED DESCRIPTION OF THE PREFERRED EMBODIMENTS

Figure 1:
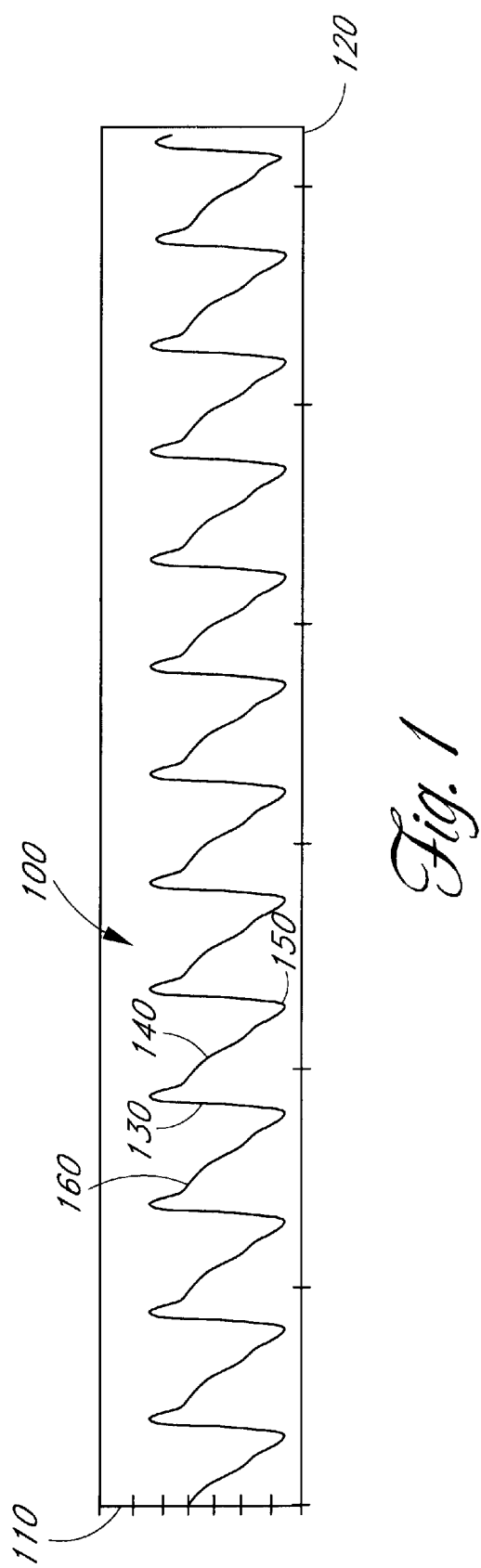
FIG. 1 illustrates a standard plethysmograph waveform that can be derived from a pulse oximeter.
Figure 2:
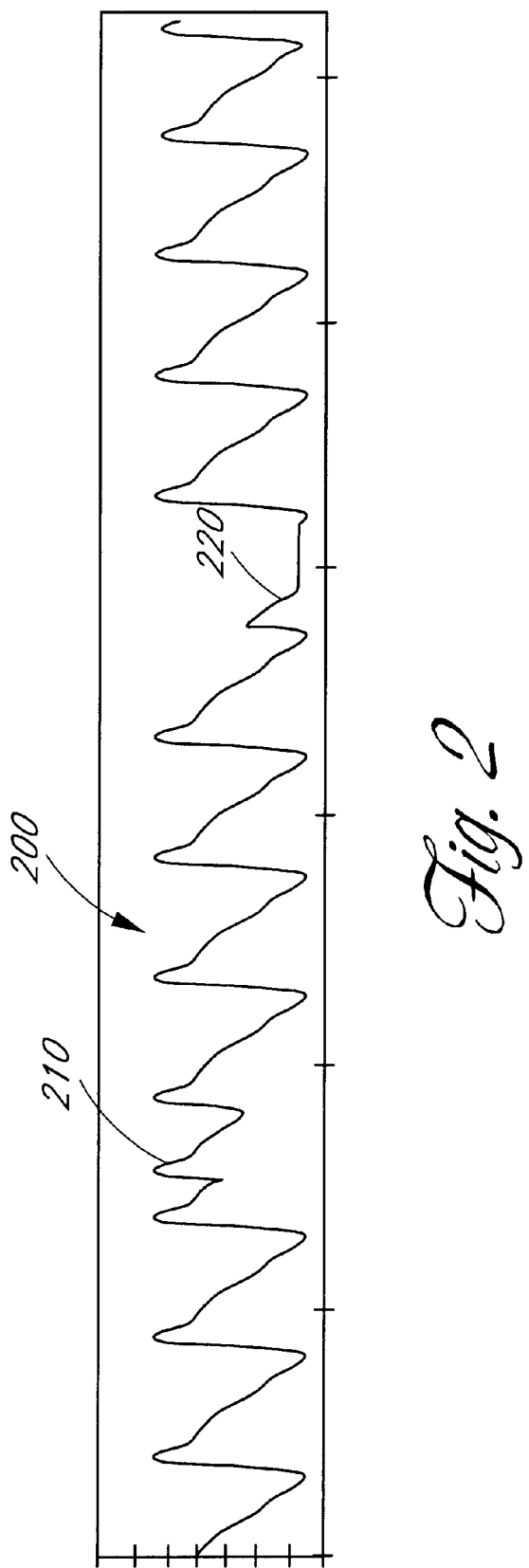
FIG. 2 illustrates a plethysmograph waveform showing an arrhythmia.
Figure 3B:
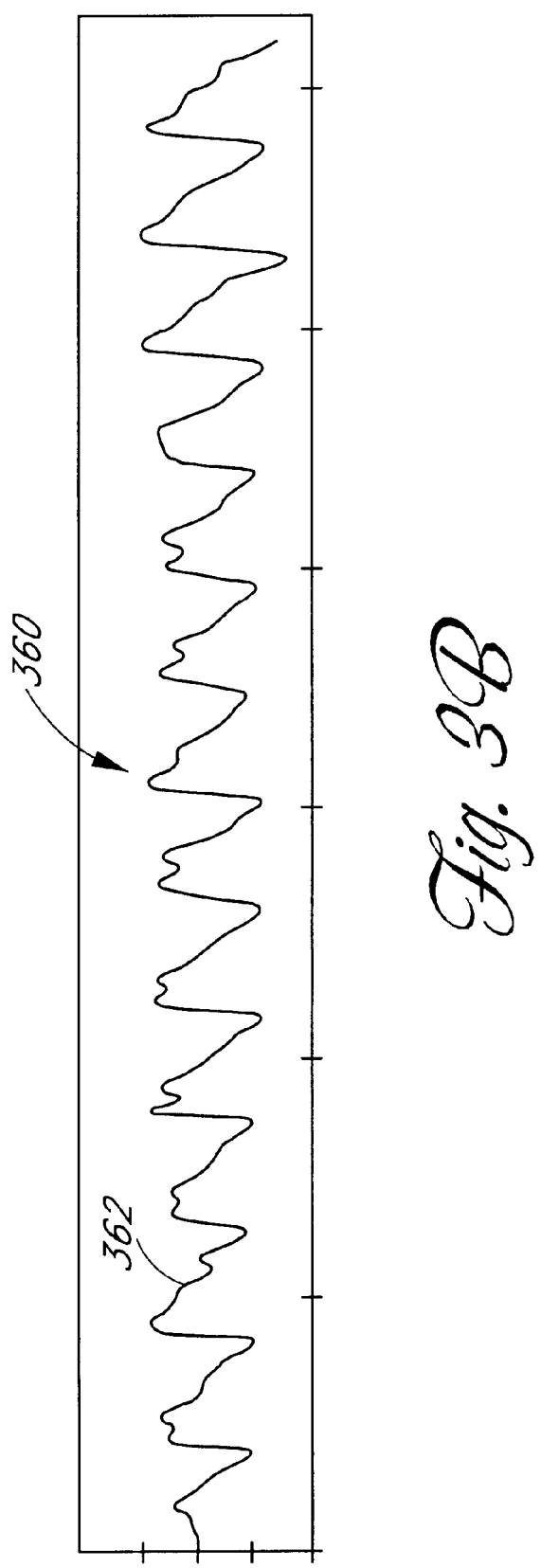
FIG. 3B illustrates a filtered plethysmograph corresponding to the distortion-corrupted plethysmograph of FIG. 3A.
Figure 4:
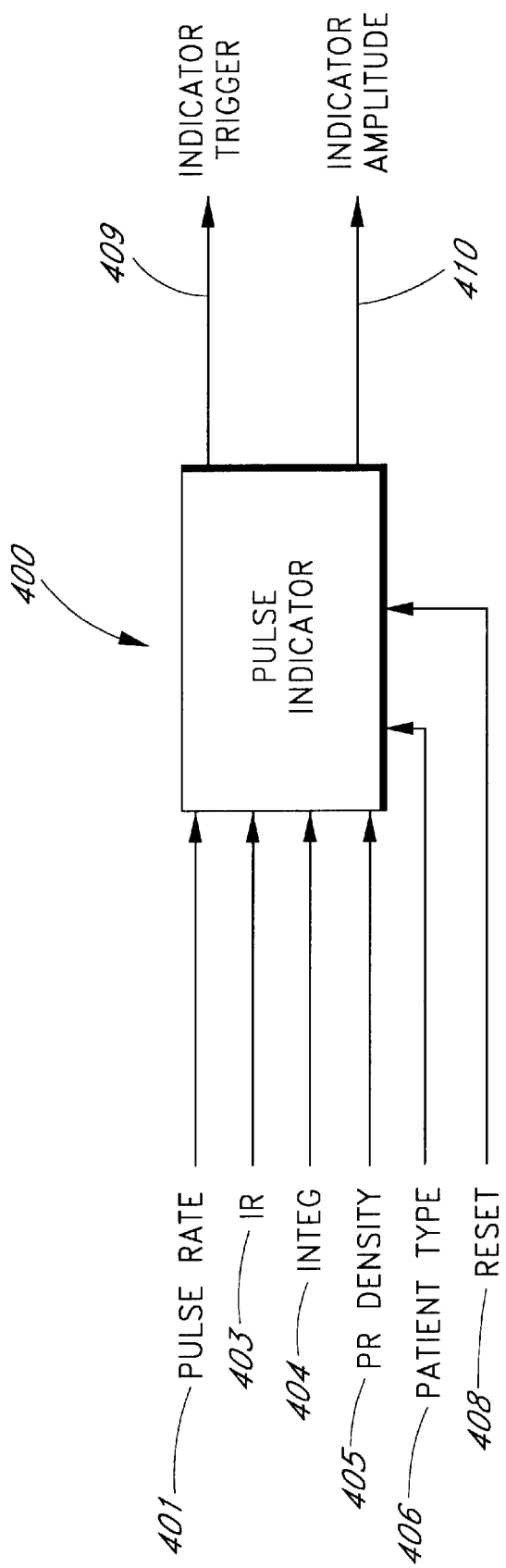
FIG. 4 illustrates the inputs and outputs of the pulse indicator according to the present invention.

FIG. 4 illustrates a pulse indicator 400, which can be incorporated into a pulse oximeter to trigger the occurrence of a synchronous indication of each of the patient's arterial pulses. The indicator 400 operates on an IR signal input 403 and generates a trigger output 409 and an amplitude output 410. The trigger output 409 can be connected to a tone generator within the pulse oximeter monitor to create a fixed-duration audible "beep" as a pulse indication. Alternatively, or in addition, the trigger output can be connected to a display generator within the pulse oximeter monitor to create a visual pulse indication. The visual pulse indication can be a continuous horizontal trace on a CRT, LCD display or similar display device, where vertical spikes occur in the trace synchronously with the patient's pulse, as described in more detail below. Alternatively, the visual pulse indication can be a bar display, such as a vertically- or horizontally-arranged stack of LEDs or similar display device, where the bar pulses synchronously with the patient's pulse.

The amplitude output 410 is used to vary the audible or visual indications so as to designate input data integrity and a corresponding confidence in the saturation and pulse rate outputs of the pulse oximeter. For example, the height of the vertical spike can be varied in proportion to the amplitude output 410, where a large or small vertical spike would correspondingly designate high or low confidence. As another example, the amplitude output 410 can be used to vary the volume of the audible beep or to change the visual indication (e.g., change color or the like) to similarly designate a high or low confidence. One of ordinary skill in the art will recognize that the trigger output 409 and amplitude output 410 can be utilized to generate a variety of audible and visual indications of a patient's pulse and data integrity within the scope of this invention.

Other inputs to the pulse indicator 400 include pulse rate 401, Integ 404, PR density 405, patient type 406 and reset 408, which are described in detail below. The beep decision involves a rule-based process that advantageously responds to the pulse waveforms of the patient's plethysmograph in low-noise or no-distortion situations, but becomes dependent an averaged pulse rate during high-noise or distortion situations. This "intelligent beep" reliably indicates the patient's pulse, yet responds to patient arrhythmias, asystole conditions and similar irregular plethysmographs.

The pulse rate input 401 to the pulse indicator 400 provides the frequency of the patient's pulse rate in beats per minute. Pulse rate can be determined as described in U.S. Pat. No. 6,002,952 "Signal Processing Apparatus and Method" or U.S. patent application Ser. No. 09/471,510 "Plethysmograph Pulse Recognition Processor," both cited above.

Figure 5A:
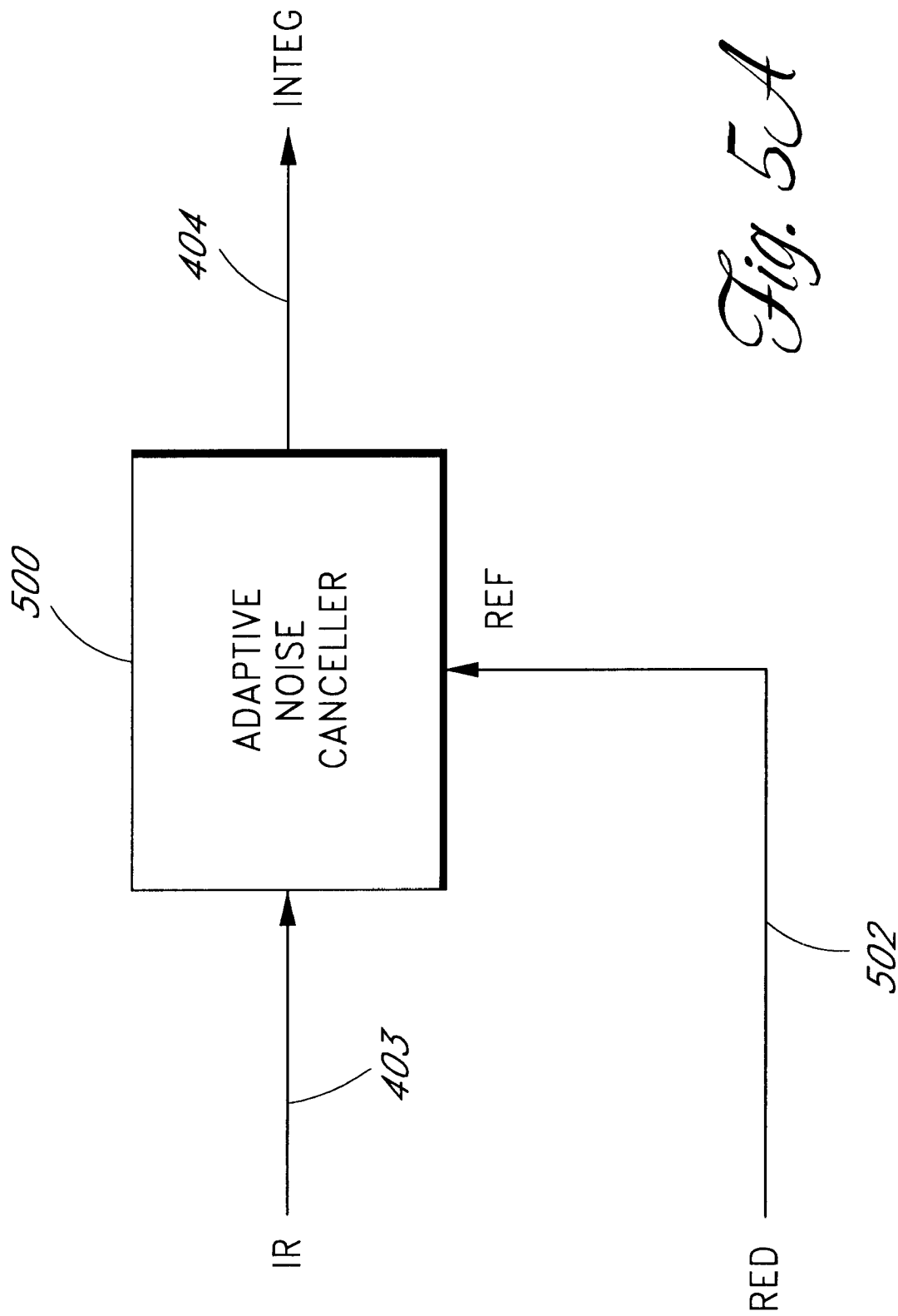
FIG. 5 illustrates the generation of one of the pulse indicator inputs.

FIG. 5A illustrates the generation of the Integ input 404 to the pulse indicator 400 (FIG. 4). The IR 403 and Red 502 signals derived from a pulse oximetry sensor are input to an adaptive noise canceller 500 having Integ 404 as an output. The Integ output 404 is a measure of the integrity of the IR 403 and Red 502 input signals.

Figure 5B:
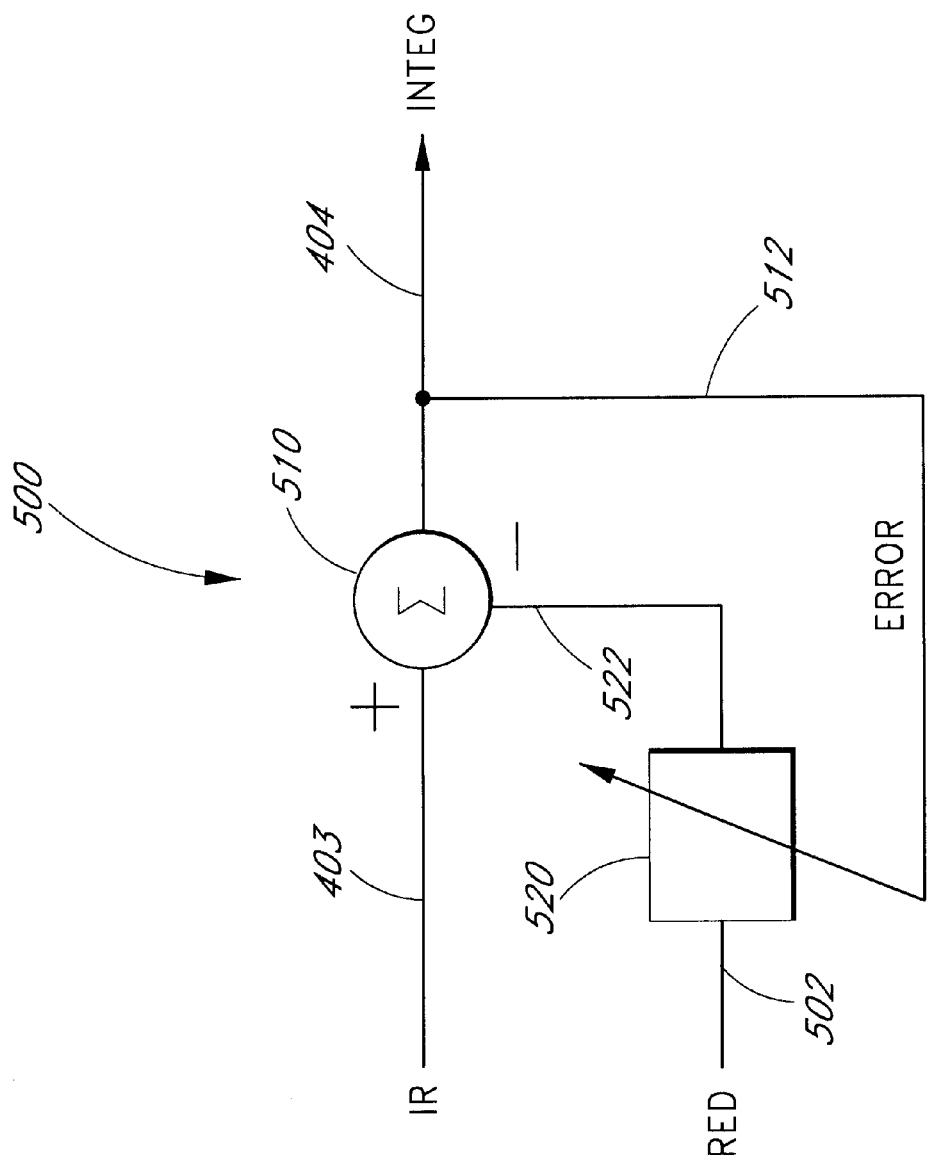

FIG. 5B illustrates the adaptive noise canceller 500. The reference input 502 is processed by an adaptive filter 520 that automatically adjusts its own impulse response through a least-squares algorithm. The least-squares algorithm responds to an error signal 512 that is the difference 510 between the noise canceller input 403 and the adaptive filter output 522. The adaptive filter is adjusted through the algorithm to minimize the power at the noise canceller output 404. If the IR 403 and Red 502 signals are relatively well-behaved with respect to the theoretical model for these signals, then the noise canceller output 404 will be relatively small. This model assumes that the same frequencies are present in the signal and noise portions of the IR and Red signals. By contrast, if a phenomenon such as scattering, hardware noise, or sensor decoupling, to name a few, affects one input signal differently than the other, then the power at the noise canceller output will be relatively large. More detail about the input signal model and the adaptive noise canceller 500 is given in U.S. Pat. No. 5,632,272 entitled "Signal Processing Apparatus," issued May 27, 1997, assigned to the assignee of the current application and incorporated by reference herein.

The PR density input 405 is a ratio of the sum of the periods of recognizable pulses within a waveform segment divided by the length of the waveform segment. This parameter represents the fraction of the waveform segment that can be classified as having physiologically acceptable pulses. In one embodiment, a segment represents a snapshot of 400 samples of a filtered input waveform, or a 6.4 second "snapshot" of the IR waveform at a 62.5 Hz sampling rate. The derivation of PR density is described in the U.S. patent application Ser. No. 09/471,510 entitled "Plethysmograph Pulse Recognition Processor," cited above.

Other inputs to the pulse indicator 400 are the IR input 403, patient type 406 and reset 408. The IR input 403 is the detected IR signal preprocessed by taking the natural logarithm, bandpass filtering and scaling in order to normalize the signal and remove the direct current component, as is well known in the art. Patient type 406 is a Boolean value that indicates either an adult sensor or a neonate sensor is in use. Reset 408 initializes the state of the pulse indicator 400 to known values upon power-up and during periods of recalibration, such as when a new sensor is attached or a patient cable is reconnected.

Figure 6:
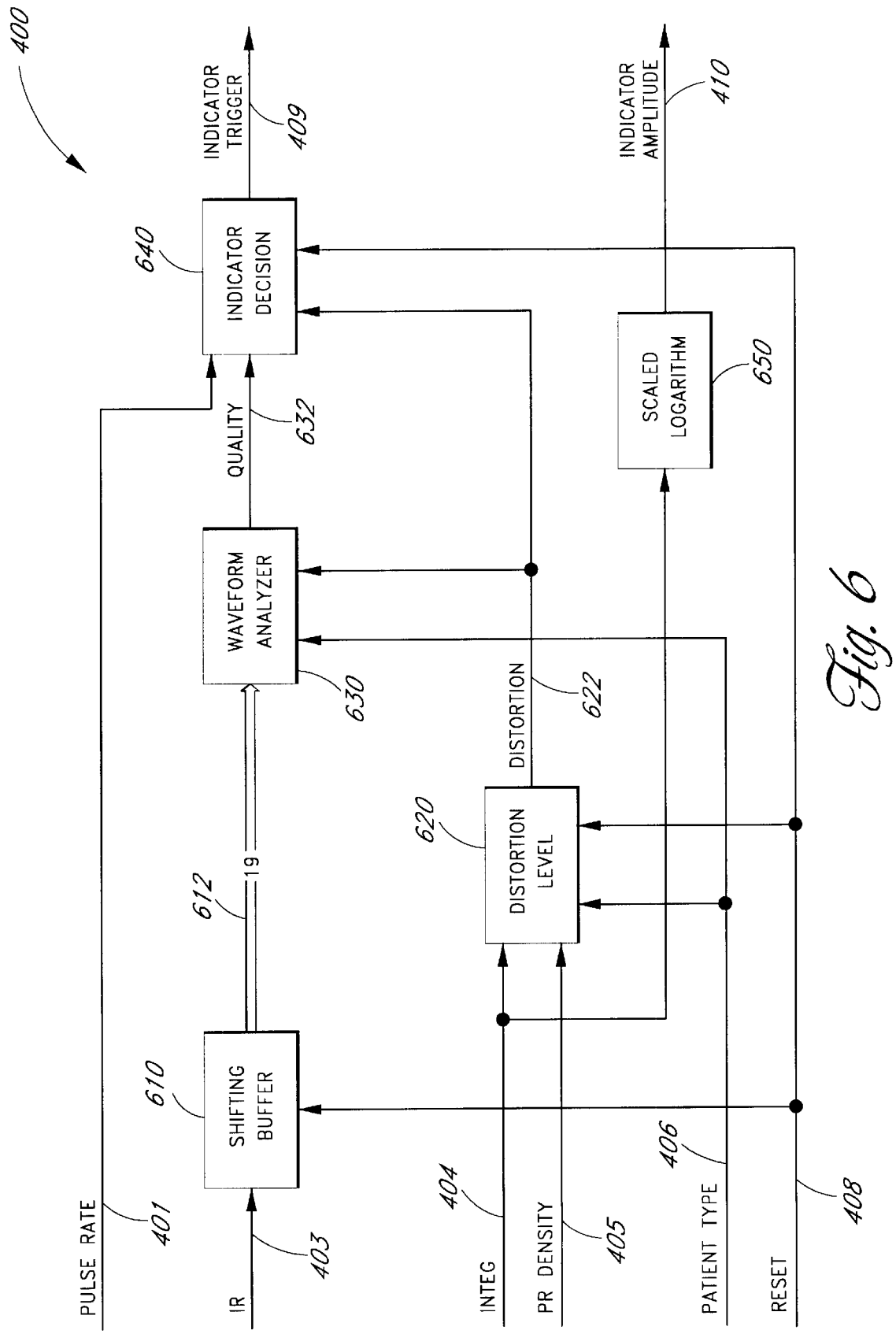
FIG. 6 is a top-level block diagram of the pulse indicator.

FIG. 6 is a functional block diagram of the pulse indicator 400. The pulse indicator 400 includes a shifting buffer 610, a distortion level function 620, a waveform analyzer 630, and a indicator decision 640, which together produce the indicator trigger 409. The pulse indicator 400 also includes a scaled logarithm function 650 that produces the indicator amplitude output 410. The shifting buffer 610 accepts the IR input 403 and provides a vector output 612 representing a fixed-size segment of the patient's plethysmograph input to the waveform analyzer 630. In a particular embodiment, the output vector is a 19 sample segment of the IR input 403. This waveform segment size represents a tradeoff between reducing the delay from pulse occurrence to pulse indicator, which is equal to 0.304 seconds at the 62.5 Hz input sample rate, yet providing a sufficiently large waveform segment to analyze. This fixed-sized segment is updated with each new input sample, and a new vector is provided to the waveform analyzer 630 accordingly.

The distortion level function 620 determines the amount of distortion present in the IR input signal 403. The inputs to the distortion level function 620 are the Integ input 404 and the PR density input 405. The distortion output 622 is a Boolean value that is "true" when distortion in the IR input 403 is above a predetermined threshold. The distortion output 622 is input to the waveform analyzer 630 and the indicator decision 640. The distortion output 622 determines the thresholds for the waveform analyzer 630, as described below. The distortion output 622 also affects the window size within which a pulse indication can occur, also described below. The distortion output 622 is also a function of the patient type input 406, which indicates whether the patient is an adult or a neonate. The reason for this dependence is also described below.

The waveform analyzer 630 determines whether a particular portion of the IR input 403 is an acceptable place for a pulse indication. The input to the waveform analyzer 630 is the vector output 612 from the shifting buffer 610, creating a waveform segment. A waveform segment portion meets the acceptance criteria for a pulse when it satisfies one of three conditions. These conditions are a sharp downward edge, a peak in the middle with symmetry with respect to the peak, and a peak in the middle with a gradual decline. If one of these criteria is met, the waveform analyzer "quality" output 632 is "true." Different criteria are applied depending on the state of the distortion output 622, which is also a waveform analyzer input. If the distortion output 622 indicates no distortion, strict criteria are applied to the waveform shape. If the distortion output 622 indicates distortion, looser criteria are applied to the waveform shape. Different criteria are also applied for waveforms obtained from adult and neonate patients, as indicated by the patient type 406. The specific criteria are described in further detail below.

The indicator decision 640 determines whether to trigger a pulse indication at a particular sample point of the input waveform. Specifically, the indicator decision 640 determines if it is the right place to trigger a pulse indication on the input waveform and if the time from the last pulse indication was long enough so that it is the right time to trigger another pulse indication. The decision as to the right place to trigger a pulse indication is a function of the analyzer output 632, which is one input to the indicator decision 640. The decision as to the right time for an indicator trigger is a function of the state of the distortion output 622, which is another input to the indicator decision 640. If the distortion output 622 is "false", i.e. no distortion is detected in the input waveform, then a fixed minimum time gap from the last indicator must occur. In a particular embodiment, this minimum time gap is 10 samples. If the distortion output 622 is "true", i.e. distortion is detected in the input waveform, then the minimum time gap is a function of the pulse rate input 401. This pulse rate dependent threshold is described in further detail below.

Figure 7:
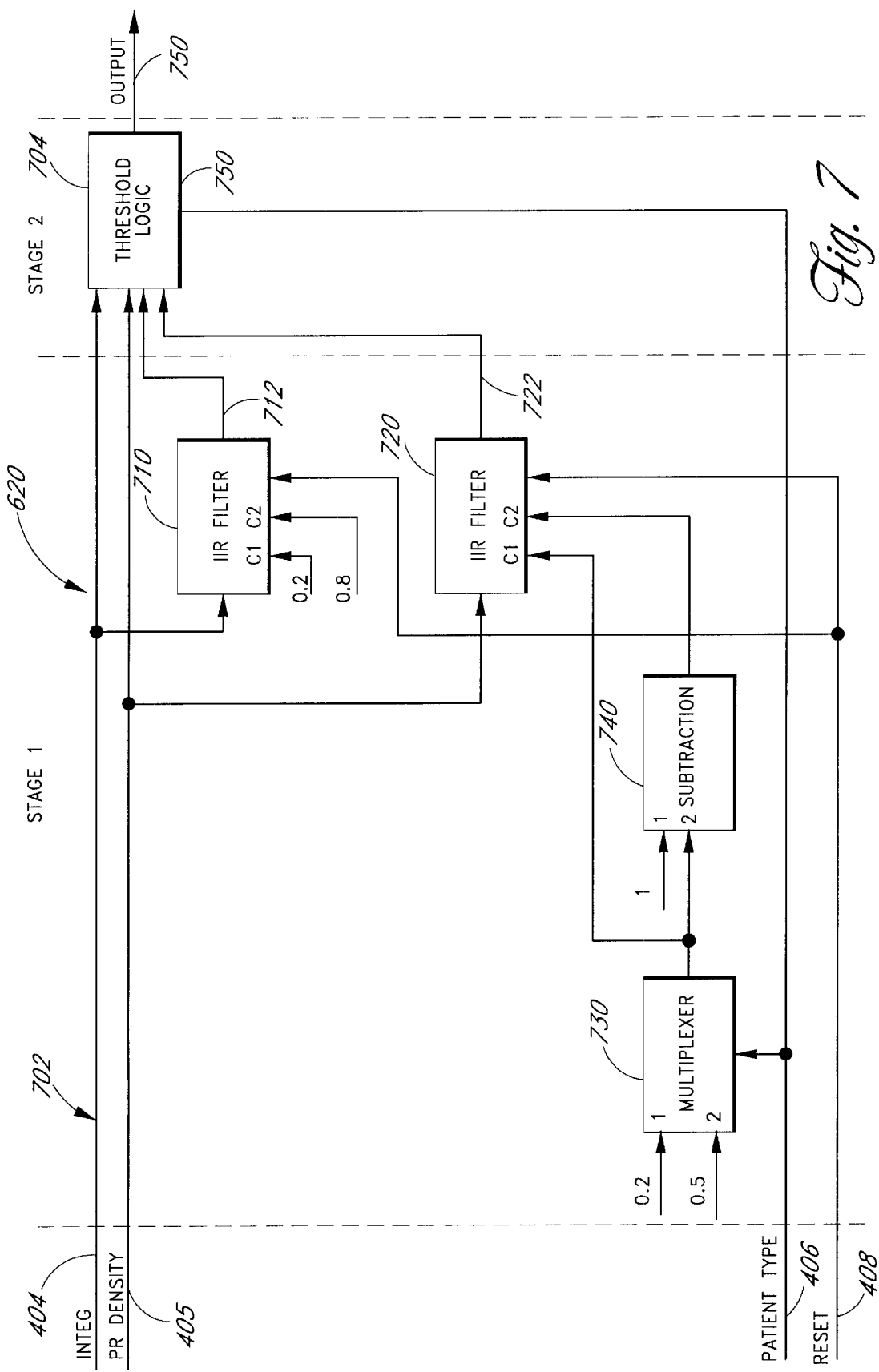
FIG. 7 is a detailed block diagram of the "distortion level" portion of the pulse indicator.

FIG. 7 is a detailed block diagram of the distortion level function 620. The distortion level function has two stages. The first stage 702 filters the Integ and PR density inputs. The second stage 704 decides whether distortion is present based on both the filtered and the unfiltered Integ input 404 and PR density 405 inputs. The first stage components are a first infinite impulse response (IIR) filter 710 for the Integ input 404 and a second IIR filter 720 for the PR density input 405.

Figure 8:
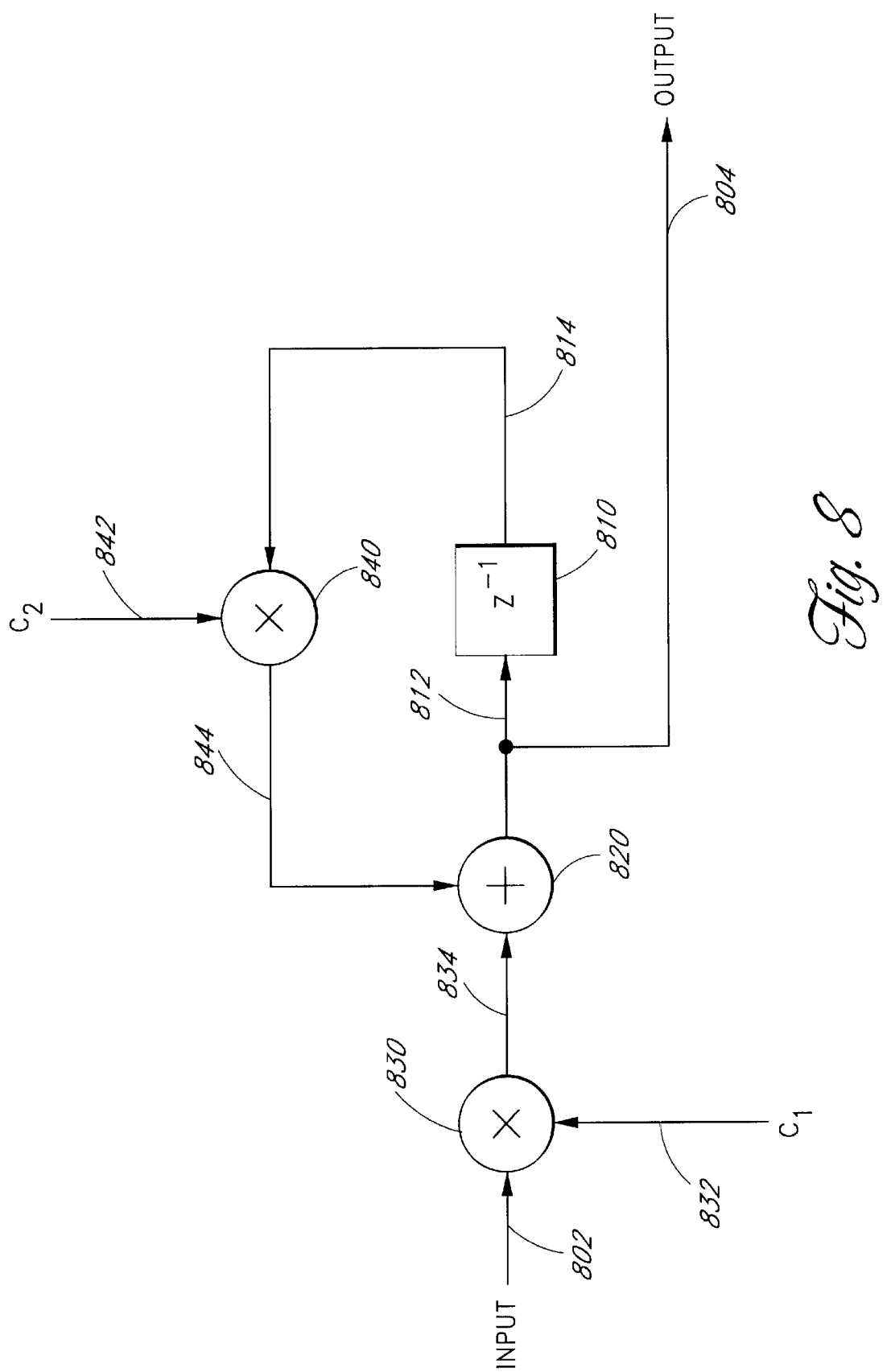
FIG. 8 is a block diagram of the infinite impulse response (IIR) filters of the "distortion level" portion illustrated in FIG. 7.

FIG. 8 illustrates the structure of the IIR filter 710, 720 (FIG. 7). Each of these filters has a delay element 810, which provides a one sample delay from the delay element input 812 to the delay element output 814. An adder 820 that sums a weighted input value 834 and a weighted feedback value 844 provides the delay element input 812. A first multiplier 830 generates the weighted input value 834 from the product of the input 802 and a first constant 832, $c_1$. A second multiplier 840 generates the weighted feedback value 844 from the product of the delay element output 814 and a second constant 842, $c_2$. With this structure, the filter output 804 is:

$$Output_n = c_1 \cdot Input_n + c_2 \cdot Output_{n-1} \quad (1)$$

That is, the nth output 804 is the weighted average of the input and the previous output, the amount of averaging being determined by the relative values of $c_1$ and $c_2$.

As shown in FIG. 7, the two IIR filters 710, 720 each apply different relative weights to the input signal. In one embodiment, the weights are fixed for the Integ filter 710 and are a function of the patient type for the PR density filter 720. In particular, for the Integ filter 710, $c_1=0.2$ and $c_2=0.8$. For the PR density filter 720, the combination of a multiplexer 730 and subtraction 740 set the values of $c_1$ and $c_2$ as a function of the patient type 406. If the signal is from an adult, then $c_1=0.2$ and $c_2=0.8$. If the signal is from a neonate, then $c_1=0.5$, $c_2=0.5$. Because a neonate pulse rate is typically higher than an adult, the PR density changes less quickly and, hence, less filtering is applied.

FIG. 7 also shows the second stage 704, which has threshold logic 750 for determining the presence of distortion. The inputs to the threshold logic 750 are Integ 404, PR density 405, filtered Integ 712 and filtered PR density 722. The threshold logic 750 is also dependent on the patient type 406. The distortion output 622 is a Boolean value that is "true" if distortion is present and "false" if no distortion is present. In one embodiment, the distortion output 622 is calculated as follows:

Adults $$\text{distortion output} = (Integ>0.01) + (\text{filtered } Integ>0.0001) \cdot (\text{filtered } PR \text{ density}<0.7) \quad (2)$$

Neonates $$\text{distortion output} = (Integ>0.05) + ((\text{filter } Integ>0.005) + (PR \text{ density}=0)) \cdot (\text{filtered } PR \text{ density}<0.8) \quad (3)$$

where a logical "and" is designated as a multiplication "·" and a logical "inclusive or" is designated as an addition "+."

Figure 9:
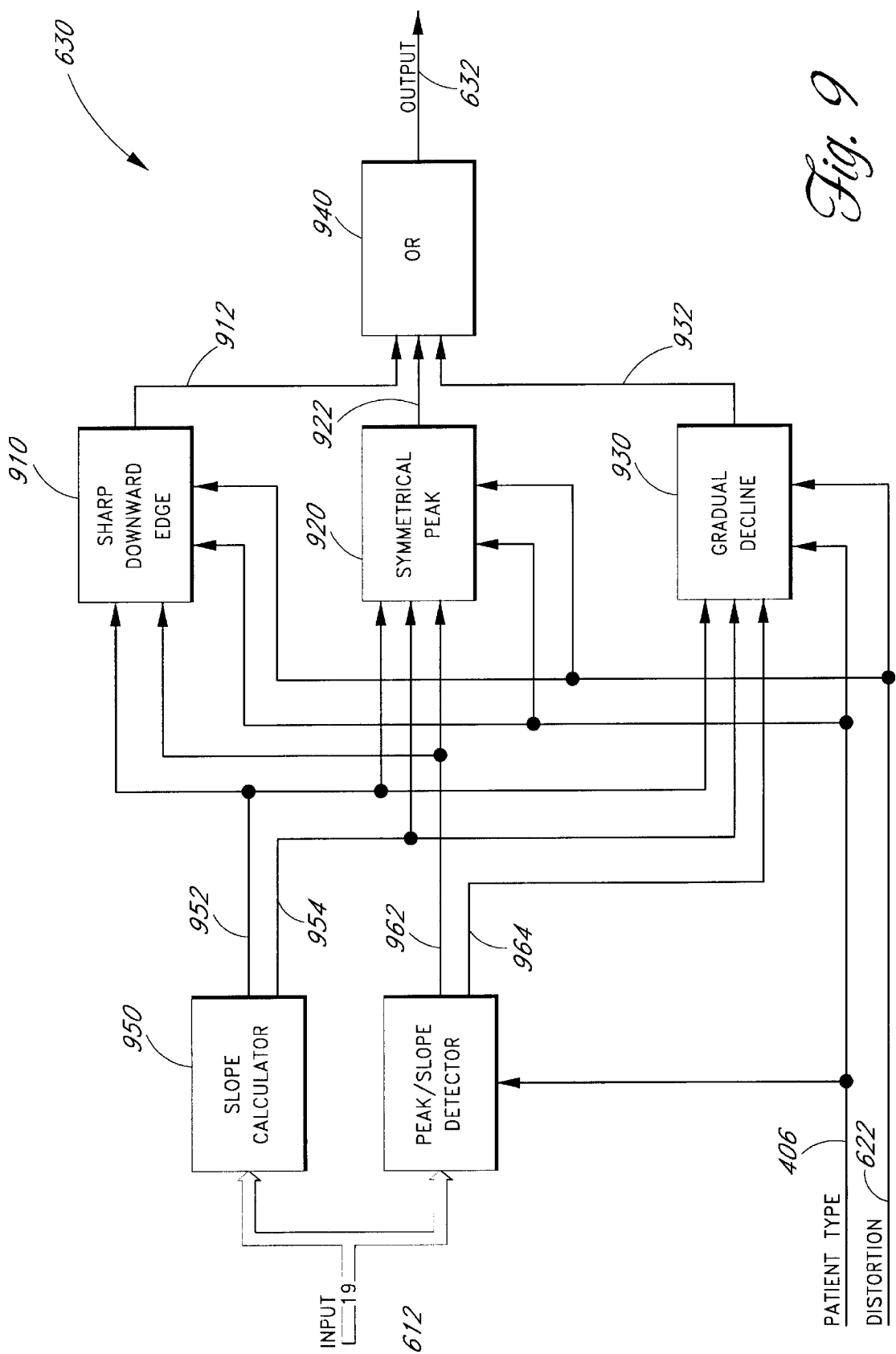
FIG. 9 is a detailed block diagram of the "waveform analyzer" portion of the pulse indicator.

FIG. 9 is a detailed block diagram of the waveform analyzer 630. As described above, the waveform analyzer 630 is based on three shape criteria, which are implemented with a sharp downward edge detector 910, a symmetrical peak detector 920 and a gradual decline detector 930. An "or" function 940 generates a waveform analyzer output 632, which has a "true" value if any of these criteria are met. The inputs to the waveform analyzer 630 are the IR waveform samples 612 from the buffer 610 (FIG. 6), patient type 406, and distortion 622 output from the distortion level function 620 (FIG. 6). The IR waveform samples 612 are a 19 sample vector representing a plethysmograph waveform segment. A slope calculator 950 and a peak/slope detector 960 provide inputs to the shape criteria components 910, 920, 930.

Figure 10:
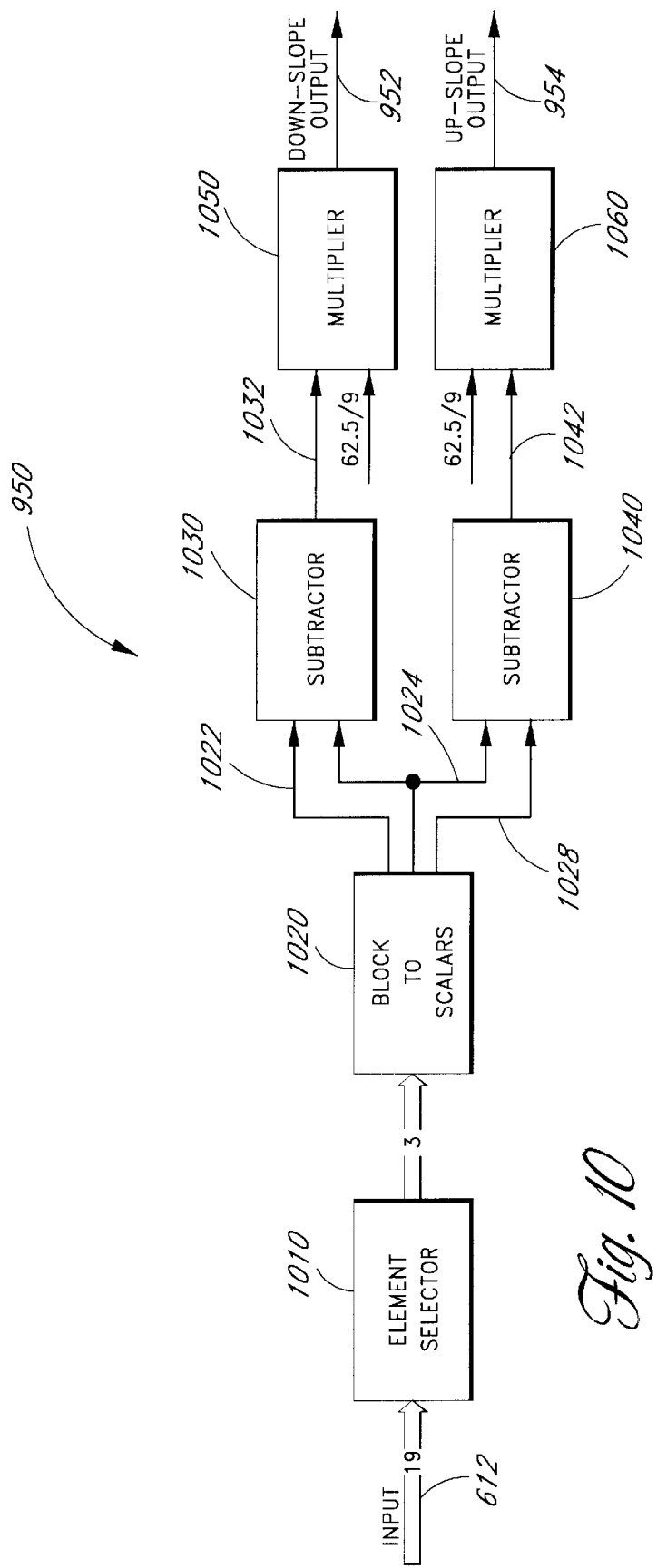
FIG. 10 is a detailed block diagram of the "slope calculator" portion of the waveform analyzer illustrated in FIG. 9.

Shown in FIG. 10, the slope calculator 950 operates on the IR waveform samples 612 to calculate a down slope value, which is provided on a down slope output 952, and an up slope value, which is provided on an up slope output 954. The down slope and up slope values are defined to be, respectively, the difference between the middle point and the last and first points, scaled by a factor of 62.5/9. The scaling factor is the sampling rate, 62.5 Hz, divided by the number of samples, 9, between the middle point and end point in the 19 sample IR waveform 612. The slope calculator 950 has an element selector 1010 that determines the center sample, the extreme left sample and the extreme right sample from the IR waveform 612. The block-to-scalars function 1020 provides a left sample output 1022 and a center sample output 1024 to a first subtractor 1030 and the center sample output 1024 and a right sample output 1028 to a second subtractor 1040. The first subtractor output 1032, which is the center value minus the right sample value, is scaled by 62.5/9 by a first multiplier 1050 that generates the down slope output 952. The second subtractor output 1042, which is the center value minus the left sample value, is scaled by 62.5/9 by a second multiplier 1060 that generates the up slope output 954.

Shown in FIG. 9, the peak/slope detector 960, like the slope calculator 950 has the IR waveform samples 612 as an input. The peak/slope detector 960 has two Boolean outputs, a peak output 962 and a slope output 964. The peak output 962 is "true" if the input waveform contains a peak. The slope output 964 is "true" if the input waveform contains a slope. The peak output 962 and slope output 964 are also dependent on the patient type 406 to the peak/slope detector 960. In one embodiment, the peak output 962 and slope output 964 are calculated as follows:

Adults $$\text{peak output} = (In_9>0) \Pi^3_{i=1}(In_7-In_{7-i}>0) \Pi^9_{i=3}(In_9-In_{9+i}>-0.005) \quad (4)$$

$$\text{slope output} = (In_9>0) \Pi^{18}_{i=3}(In_{i-1}-In_i>-0.005) \quad (5)$$

Neonates $$\text{peak output} = \Pi^3_{i=1}(In_7-In_{7-i}>0) \Pi^9_{i=3}(In_9-In_{9+i}>-0.005) \quad (6)$$

$$\text{slope output} = \Pi^{18}_{i=3}(In_{i-1}-In_i>-0.005) \quad (7)$$

where $In_i$ is the ith waveform sample in the 19 sample IR waveform 612.

FIG. 9 shows the sharp downward edge detector 910, which is the sub-component of the waveform analyzer 630 that determines whether the shape of the input waveform segment meets the sharp downward edge criteria. To do this, the edge detector 910 determines whether the down slope value is bigger than a certain threshold and whether a peak is present. The edge detector 910 has as inputs the down slope output 952 from the slope calculator 950, the peak output 962 from the slope/peak detector 960, the distortion output 622 from the distortion level function 620 (FIG. 6) and the patient type 406. The edge detector output 912 is a Boolean value that is "true" when the waveform shape criteria is met. In one embodiment, the edge detector output 912 is calculated as follows:

Adults and No Distortion $$\text{edge output} = (\text{down slope output}>3) \cdot \text{peak output} \quad (8)$$

Neonates and No Distortion $$\text{edge output} = (\text{down slope value}>1) \cdot \text{peak output} \quad (9)$$

Distortion (Adults or Neonates)

$$\text{edge output} = (\text{down slope value}>0.65) \cdot \text{peak output} \quad (10)$$

FIG. 9 also shows the symmetrical peak detector 920, which is the sub-component of the waveform analyzer 630 that determines whether the waveform contains a symmetrical peak. To do this, the symmetrical peak detector 920 checks whether the down slope and up slope values are bigger than a certain threshold, if the difference between their magnitudes is small, and if a peak is present. The symmetrical peak detector 920 has as inputs the down slope output 952 and the up slope output 954 from the slope calculator 950, the peak output 962 from the slope/peak detector 960, the distortion output 622 from the distortion level function 620 (FIG. 6) and the patient type 406. The symmetrical peak output 922 is a Boolean value that is "true" when the waveform shape criteria is met. In one embodiment, the symmetrical peak output 922 is defined as follows:

Adults $$\text{symmetrical peak output=false} \tag{11}$$

Neonates and No Distortion $$\text{symmetrical peak output=(down slope>1)·(up slope>1)·(|down slope−up slope|} \leq 0.5)\cdot\text{peak} \tag{12}$$

Neonates and Distortion $$\text{symmetrical peak output=(down slope>0.35)·(up slope>0.35)·(|down slope−up slope|} \leq 0.5)\cdot\text{peak} \tag{13}$$

FIG. 9 further shows the gradual decline detector 930, which is the sub-component of the waveform analyzer 630 that determines whether the waveform contains a gradual decline. To do this, the decline detector 930 checks whether the difference between the down slope and the up slope values is in between two thresholds and if a slope is present. The decline detector 930 has as inputs the down slope output 952 and the up slope output 954 from the slope calculator 950, the slope output 964 from the slope/peak detector 960, the distortion output 622 from the distortion level function 620 (FIG. 6) and the patient type 406. The decline output 932 is a Boolean value that is "true" when the waveform shape criteria is met. In one embodiment, the decline output 932 is defined as follows:

Adults and No Distortion $$\text{decline=(3<(down slope−up slope)<6)·slope} \tag{14}$$

Neonates and No Distortion $$\text{decline=(0.5<(down slope−up slope)<2)·slope} \tag{15}$$

Distortion (Adults or Neonates)

$$\text{decline=(0.5<(down slope−up slope)<8)·slope} \tag{16}$$

Figure 11:
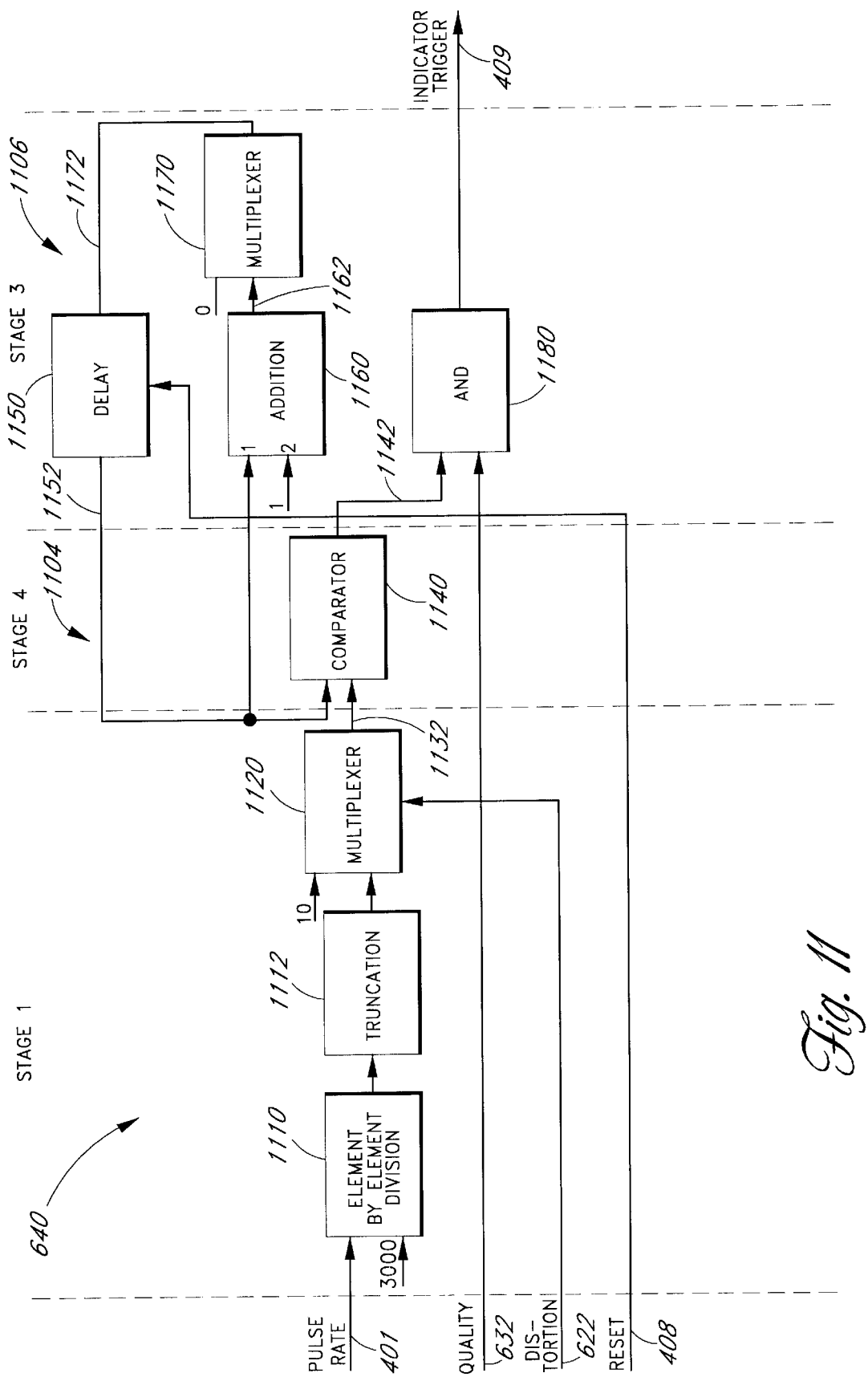
FIG. 11 is a detailed block diagram of the "indicator decision" portion of the pulse indicator.

FIG. 11 is a detailed block diagram of the indicator decision 640 sub-component. The first stage 1102 of the indicator decision 640 determines a minimum time gap after which a pulse indicator can occur. The second stage 1104 determines whether the number of samples since the last indicator is greater than the minimum allowed pulse gap. The third stage 1106 decides whether to generate a pulse indicator trigger. If no trigger occurs, a sample count is incremented. If an indicator trigger occurs, the sample count is reset to zero.

As shown in FIG. 11, the first stage 1102 has a divider 1110, a truncation 1120 and a first multiplexer 1130. These components function to set the minimum allowable gap between pulse indications. Under no distortion, the minimum gap is 10 samples. Under distortion, the gap is determined by the pulse rate. Specifically, under distortion, the minimum gap is set at 80% of the number of samples between pulses as determined by the pulse rate input 401. This is computed as 0.8 times the sample frequency, 62.5 Hz., divided by the pulse rate in pulses per second, or:

$$\text{min. gap=0.8×(60/pulse rate)×62.5=3000/pulse rate} \tag{17}$$

The divider 1110 computes 3000/pulse rate. The divider output 1112 is truncated 1120 to an integer value. The first multiplexer 1130 selects the minimum gap as either 10 samples if the distortion input 622 is "false" or the truncated value of 3000/pulse rate if the distortion input 622 is "true." The selected value is provided on the multiplexer output 1132, which is fed to the second stage 1104. The second stage 1104 is a comparator 1140, which provides a Boolean output 1142 that is "true" if a counter output 1152 has a value that is equal to or greater than the minimum gap value provided at the first multiplexer output 1132.

FIG. 11 also illustrates the third stage 1106, which has a counter and an "and" function. The counter comprises a delay element 1150 providing the counter output 1152, an adder 1160 and a second multiplexer 1170. When the counter is initialized, the second multiplexer 1170 provides a zero value on the multiplexer output 1172. The multiplexer output 1172 is input to the delay element, which delays the multiplexer output value by one sample period before providing this value at the counter output 1152. The counter output 1152 is incremented by one by the adder 1160. The adder output 1162 is input to the second multiplexer 1162, which selects the adder output 1162 as the multiplexer output 1172 except when the counter is initialized, as described above. The counter is initialized to zero when the pulse indicator trigger 409 is "true" as determined by the output of the "and" element 1180. The "and" 1180 generates a "true" output only when the comparator output 1142 is "true" and the quality output 632 from the waveform analyzer 630 (FIG. 6) is also "true."

Visual Pulse Indicator

With motion, a plethysmograph displayed on a pulse oximeter is often distorted and may be obscured by artifact. With the advent of pulse oximeters that can accurately calculate saturation during motion, the plethysmograph alone is not a sufficient indicator of arterial pulses or signal quality. A visual pulse indicator according to the present invention can supplement the plethysmograph display to identify the occurrence of a patient's pulse and also indicate confidence in the computed values of saturation and pulse rate. The visual pulse indicator, shown as vertical lines coinciding with the peak of arterial pulsations, indicates a patient's pulse even when the plethysmograph is distorted or obscured by artifact. The height of the vertical line indicates data integrity. A high vertical line indicates confidence in the saturation and pulse rate measurements, whereas a small vertical bar indicates lowered confidence.

Figure 12:
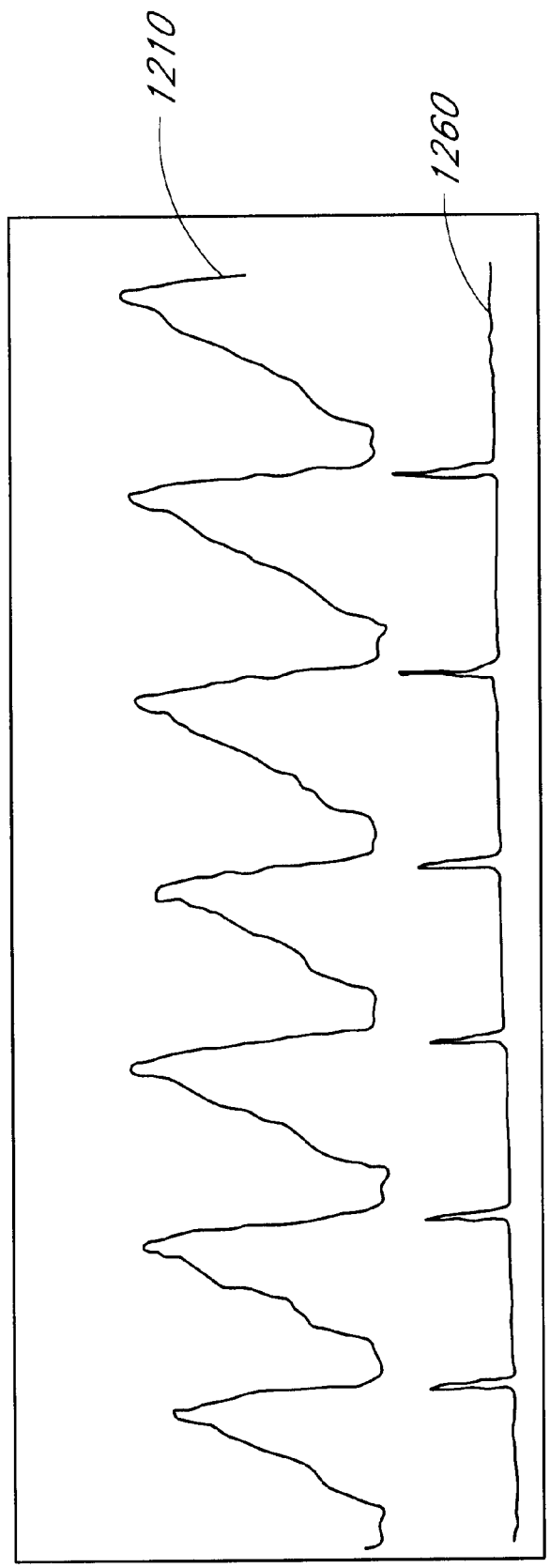
FIG. 12 is a display illustrating a normal plethysmograph and a corresponding visual pulse indicator.
Figure 13:
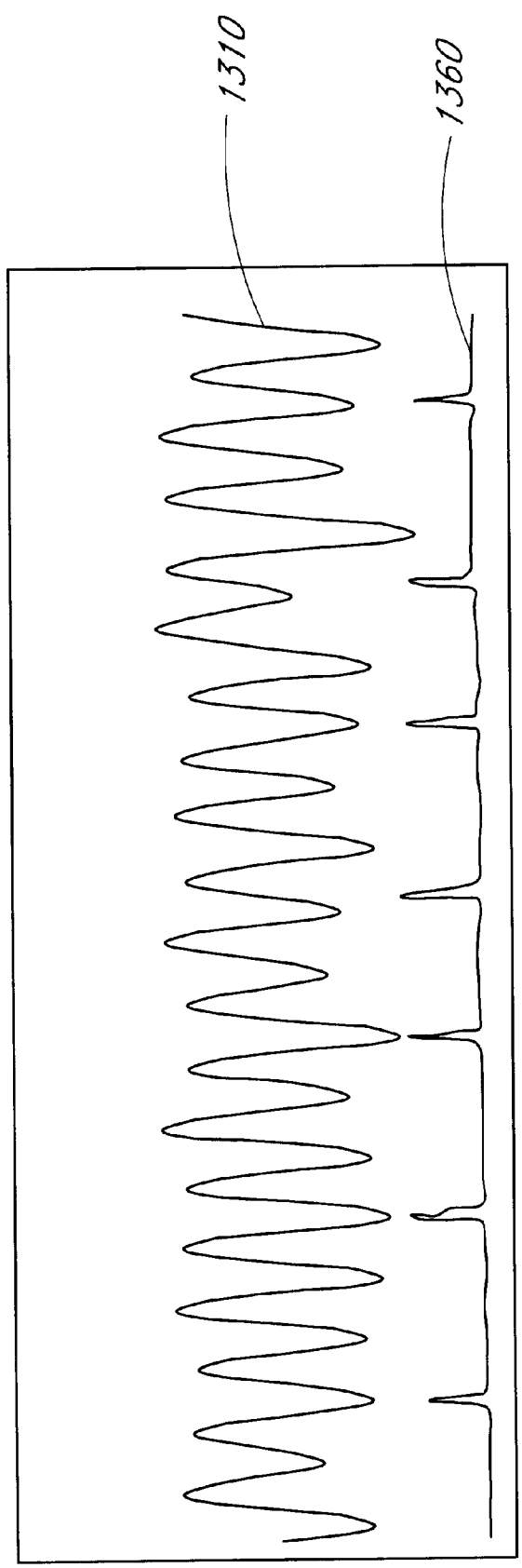
FIG. 13 is a display illustrating a distorted plethysmograph and a corresponding high-confidence-level visual pulse indicator.
Figure 14:
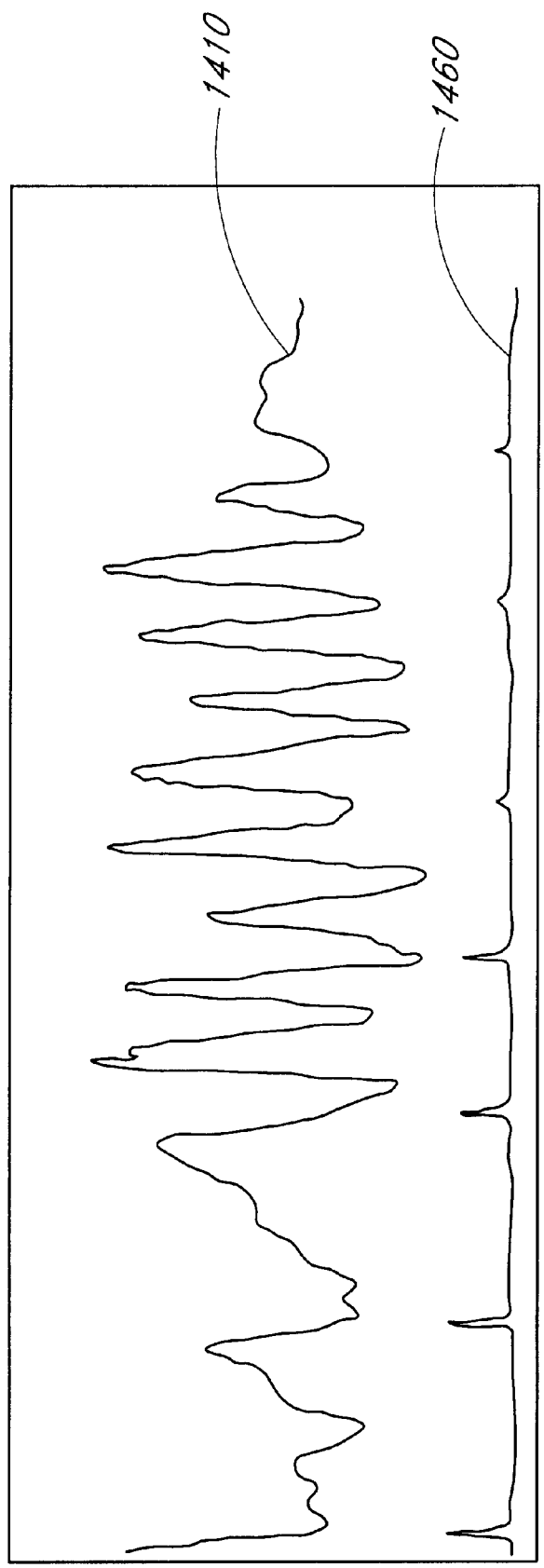
FIG. 14 is a display illustrating a distorted plethysmograph and a corresponding low-confidence-level visual pulse indicator.

FIGS. 12–14 illustrate a visual pulse indicator generated in response to the indicator trigger output 409 (FIG. 4) and indicator amplitude output 410 of the pulse indicator 400 (FIG. 4). In FIG. 12, the top trace 1210 is an exemplar plethysmograph waveform without significant distortion. The bottom trace 1260 is a corresponding visual pulse indication comprising a series of relatively large amplitude spikes that are generally synchronous to the falling edges of the input waveform 1210. Because the input waveform 1210 has low distortion, the pulse indication 1260 is somewhat redundant, i.e. pulse occurrence and data confidence is apparent from the input waveform alone. Nevertheless, FIG. 12 illustrates the visual pulse indicator according to the present invention.

In FIG. 13, the plethysmograph waveform illustrated in the top trace 1330 displays significant distortion. In contrast to the example of FIG. 12, pulse occurrence and data confidence is not obvious from the input waveform alone. The corresponding visual pulse indicator 1360, however, indicates pulse occurrence at the location of the display spikes. Further, the relatively large spike amplitude indicates high data integrity and a corresponding high confidence in the computed values of pulse rate and saturation despite the waveform distortion.

In FIG. 14, the plethysmograph waveform 1410 also displays significant distortion. In contrast to the example of FIG. 13, the visual pulse indicator 1460 displays relatively low amplitude spikes corresponding to the latter half of the waveform sample, indicating relatively low data integrity and low confidence in the computed pulse rate and saturation.

Signal Quality Alert

Figure 15:
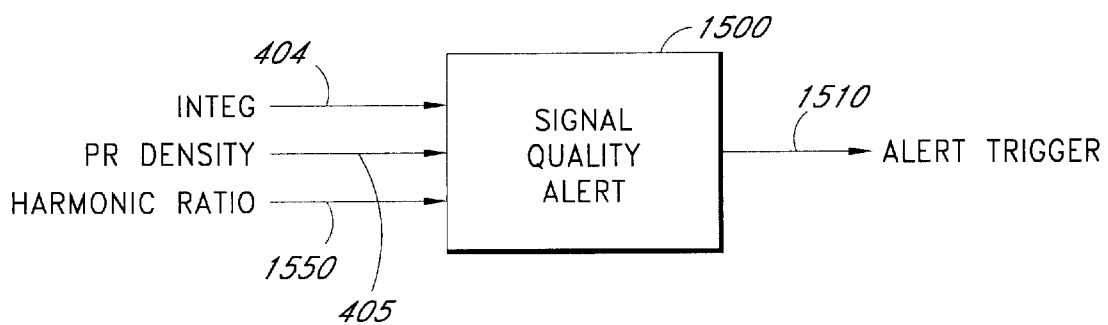
FIG. 15 is an input and output block diagram of a signal quality alert.
Figure 16:
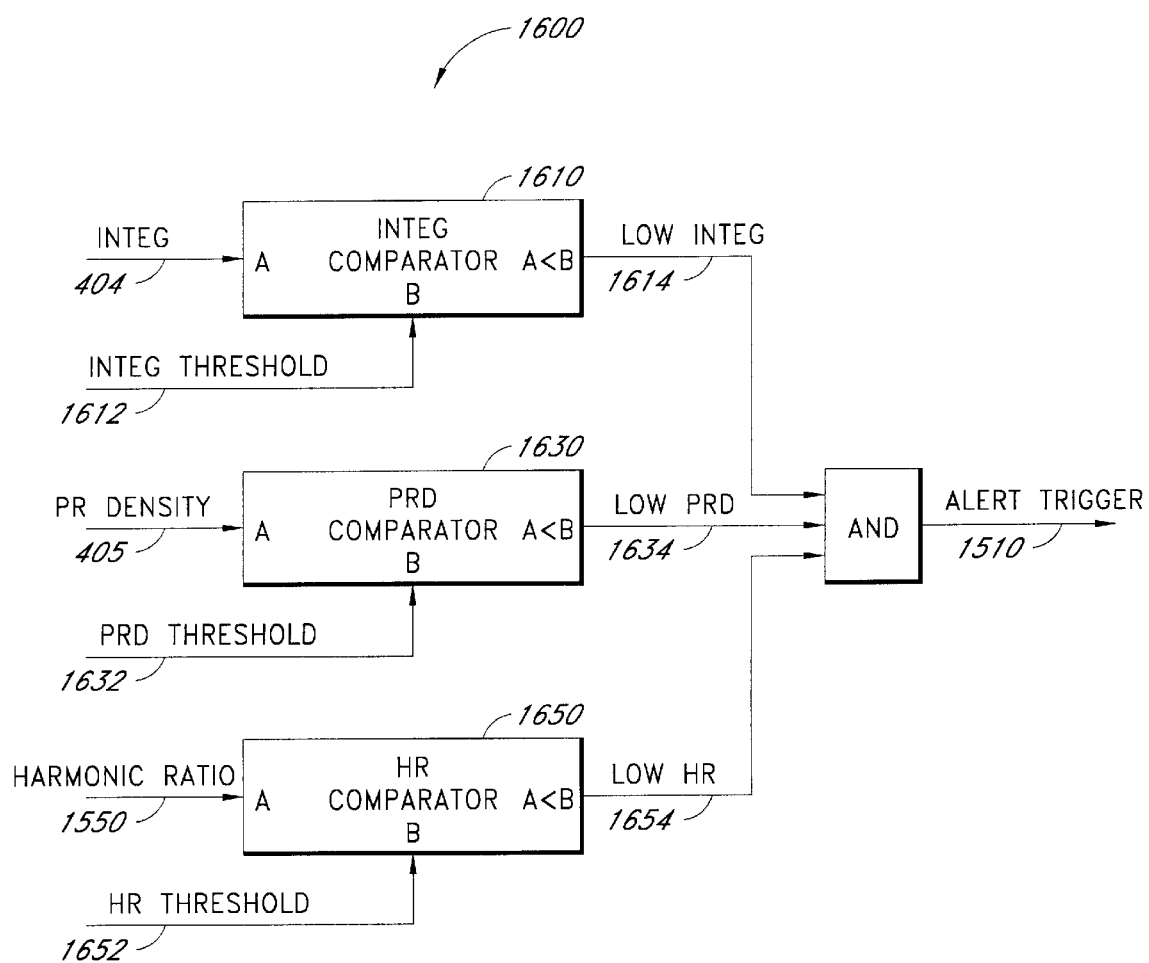
FIG. 16 is a functional block diagram of a signal quality alert.

FIGS. 15–16 illustrate the generation of a caregiver alert that supplements the visual pulse indicator described with respect to FIGS. 12–14, above. When signal quality is very low, the accuracy of the computed pulse rate and saturation may be compromised and a caregiver warning is warranted. The alert may be a display message, an alarm having a unique tone or some other form of visual or audible method of drawing the attention of the caregiver.

As shown in FIG. 15, a signal quality alert 1500 has an alert trigger output 1510 and integ 404, PR density 405 and harmonic ratio 1550 inputs. Integ 404 and PR density 405 are described with respect to FIG. 4, above. The harmonic ratio 1550 is derived from the ratio of the plethysmograph signal energy contained in frequency bands around the heart rate fundamental frequency and its harmonics divided by the total signal energy. The harmonic ratio provides a measure of signal quality because most of the signal energy in an uncorrupted plethysmograph is at the heart rate and harmonics. The plethysmograph spectrum and associated frequency measurements are described in U.S. Pat. No. 6,002,952, cited above.

As shown in FIG. 16, the signal quality alert 1500 has an integrity (INTEG) comparator 1610, a PR density (PRD) comparator 1630 and a harmonic ratio (HR) comparator 1650. Each of the comparators 1610, 1630, 1650 has a Boolean output 1614, 1634, 1654 that is asserted when an input signal quality measure 404, 405, 1550 falls below a corresponding threshold 1612, 1632, 1652. In particular, the INTEG comparator 1610 has a low INTEG output 1614 that is asserted when signal integrity falls below the INTEG threshold 1612. Also, the PRD comparator 1630 has a low PRD output 1634 that is asserted when the PR density 405 falls below the PR density threshold 1632. Further, the HR comparator 1650 has a low HR output 1654 that is asserted when the harmonic ratio 1550 falls below the HR threshold 1652.

Also shown in FIG. 16, the comparator outputs 1614, 1634, 1654 are combined with a logical AND to generate an alert trigger output 1510. In particular, the alert trigger output 1510 is a Boolean value asserted when all of the low signal quality outputs 1614, 1634, 1654 are asserted. In this manner, the alert trigger 1510 is responsive to a combination of signal quality measures 404, 405, 1550 and is triggered when these measures all indicate a very low signal quality, as determined by the threshold inputs 1612, 1632, 1652. In one embodiment, each of the signal quality measures 404, 405, 1550 vary between 0 and 1, and the INTEG threshold 1612 is set at 0.3; the PRD threshold 1632 is set at 0.7 and the HR threshold 1652 is set at 0.8.

Although the signal quality alert has been described with respect to a combination of the signal quality measures integrity, pulse rate density and harmonic ratio, the signal quality alert could also be triggered based upon other measures related to the level of signal distortion or corruption, motion artifact, or noise. Further, although the signal quality alert has been described with respect to a logical AND combination of these signal quality measures compared with corresponding thresholds, various other combinations of these or other measures related to the level of signal distortion or corruption, motion artifact, or noise could be used to trigger a signal quality alert. For example, an OR combination of signal quality measures each compared to a different threshold could be used to trigger an alert. As another example, an arithmetic combination of signal quality measures could be compared to a single threshold to trigger an alert. As a further example, the height of the displayed visual pulse indicator could trigger a signal quality alert if sufficiently less than full-scale, such as less than one-third full-scale.

Confidence-Based Alarm

Figure 17:
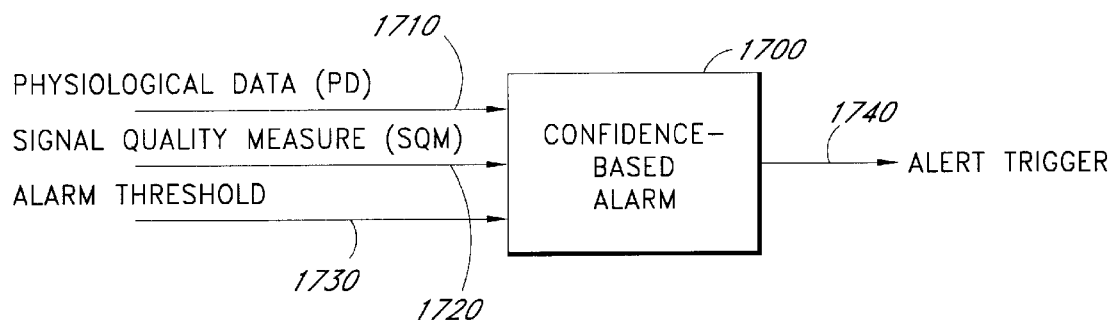
FIG. 17 is an input and output block diagram of a confidence-based alarm.
Figure 18:
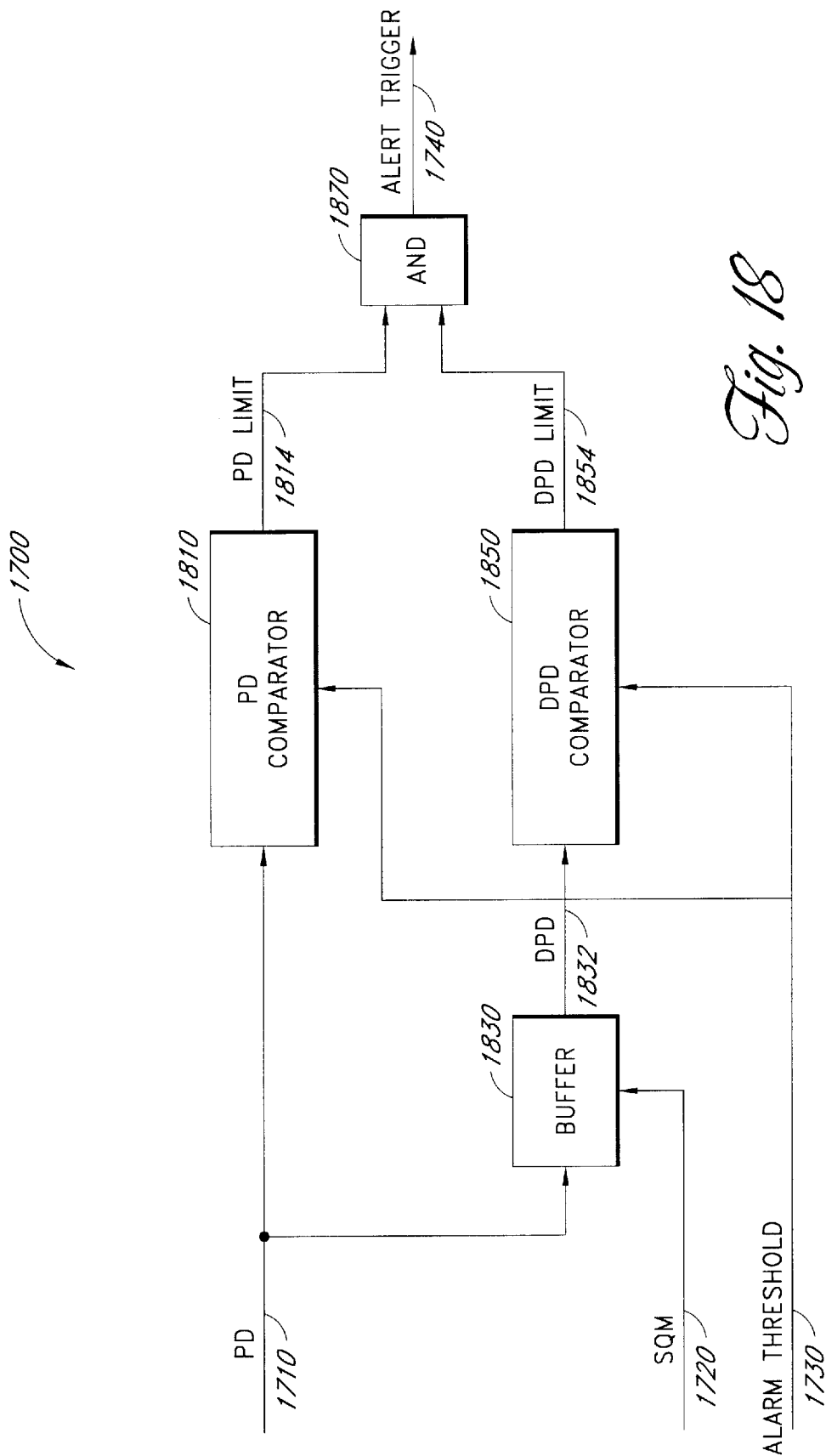
FIG. 18 is a functional block diagram of a confidence-based alarm.

FIGS. 17–18 illustrate a confidence-based alarm responsive to physiological data, such as oxygen saturation or pulse rate. The confidence-based alarm 1700 according to the present invention is adapted to reduce the probability of missed true alarms during high data confidence periods and to reduce the probability of false alarms during low data confidence periods. As shown in FIG. 17, the confidence-based alarm 1700 has as inputs physiological data (PD) 1710, signal quality measure (SQM) 1720, and alarm threshold 1730 and an alarm trigger output 1740. The PD input 1710 may be, for example, saturation or pulse rate data. The SQM input 1720 may be data integrity, pulse rate density, harmonic ratio, or other measures or combinations of measures related to the level of signal distortion or corruption, motion artifact, or noise. The alarm trigger 1740 initiates an audio and/or visual warning that alerts a caregiver whenever the physiological data indicates a patient's vital signs are outside of acceptable limits, as set by the alarm threshold 1730, for example a minimum saturation or a maximum or minimum pulse rate. There may be one or more alarms 1700 in a particular pulse oximeter.

As shown in FIG. 18, the confidence-based alarm 1700 has an PD comparator 1810, a data buffer 1830 and a delayed PD (DPD) comparator 1850. The PD comparator 1810 has PD 1710 and alarm threshold 1730 inputs and a PD limit 1814 output. The PD limit 1814 is a Boolean value that is asserted when the PD input 1710 exceeds, either above or below depending on the physiological measure, the alarm threshold 1730. The data buffer 1830 acts as a delay line, time shifting the PD data 1710 by a value that is a function of the SQM input 1720 to generate the delayed PD (DPD) data 1832. The DPD comparator has DPD 1832 and alarm threshold 1730 inputs and a DPD limit 1854 output. The DPD limit 1854 is a Boolean value that is asserted when the DPD input 1832 exceeds the alarm threshold input 1730, similar to the PD limit 1814. In an alternative embodiment, the threshold inputs to the PD comparator 1810 and the DPD comparator 1850 are set to different levels. The confidence-based alarm 1700 also has a logical AND that combines the PD limit 1814 and DPD limit 1854 outputs to generate the alarm trigger 1740. The alarm trigger 1740 is a Boolean value that is asserted when both the PD limit 1814 and the DPD limit 1854 are asserted.

Also shown in FIG. 18, the confidence-based alarm 1700 rejects those features of the physiological data PD 1710 that are below the alarm limit for less duration than the data buffer 1830 delay, so as to reduce false alarms. The probably of false alarms is reduced with increasing data buffer 1830 delay. Generally, reducing the probability of false alarms increases the probability of missed true alarms. Advantageously, the buffer delay is a function of a signal quality measure 1720, so that the probability of false alarms is reduced when signal quality is low and the probability of missed true alarms is reduced when signal quality is high.

Figure 19B:
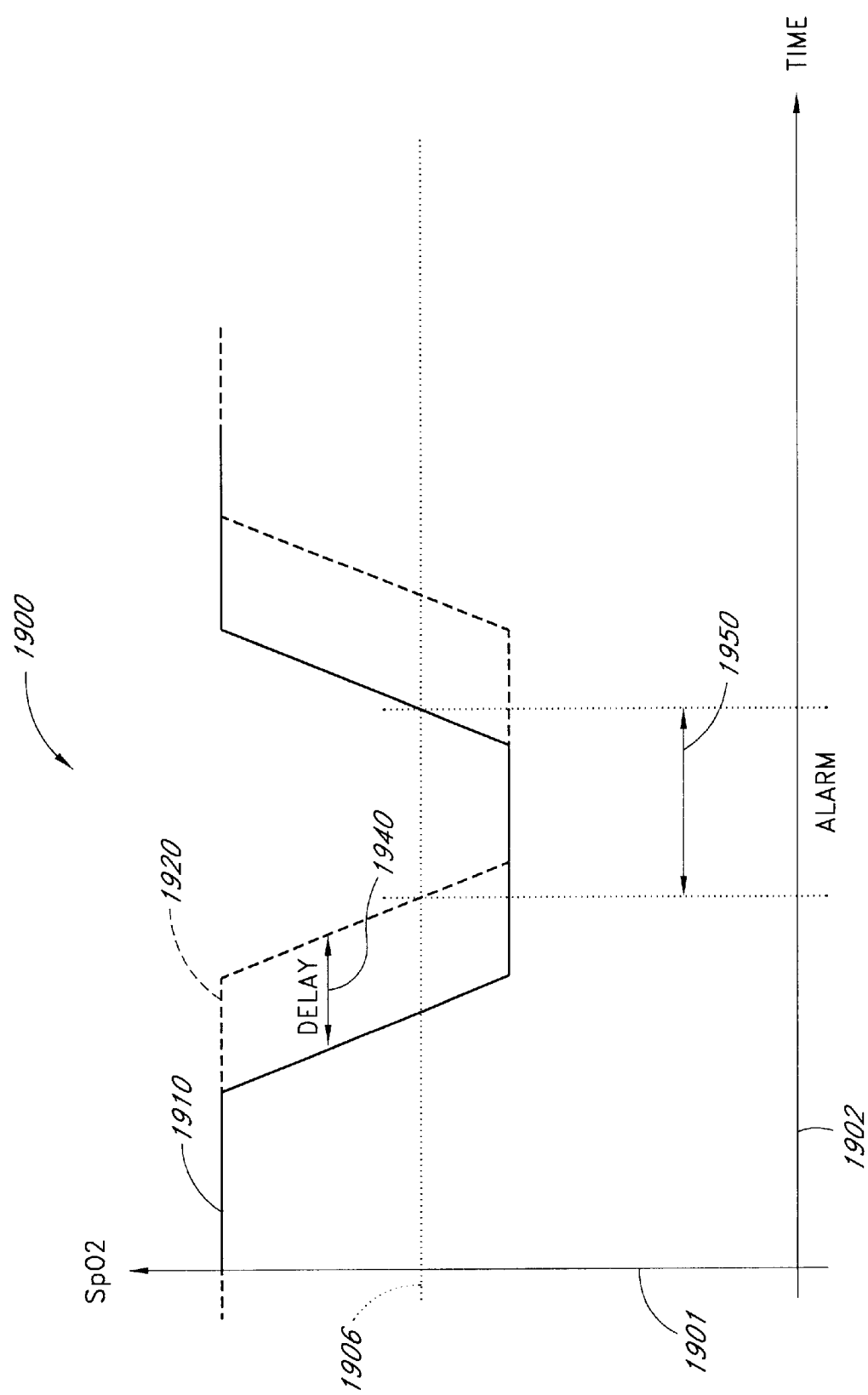
Figure 19D:
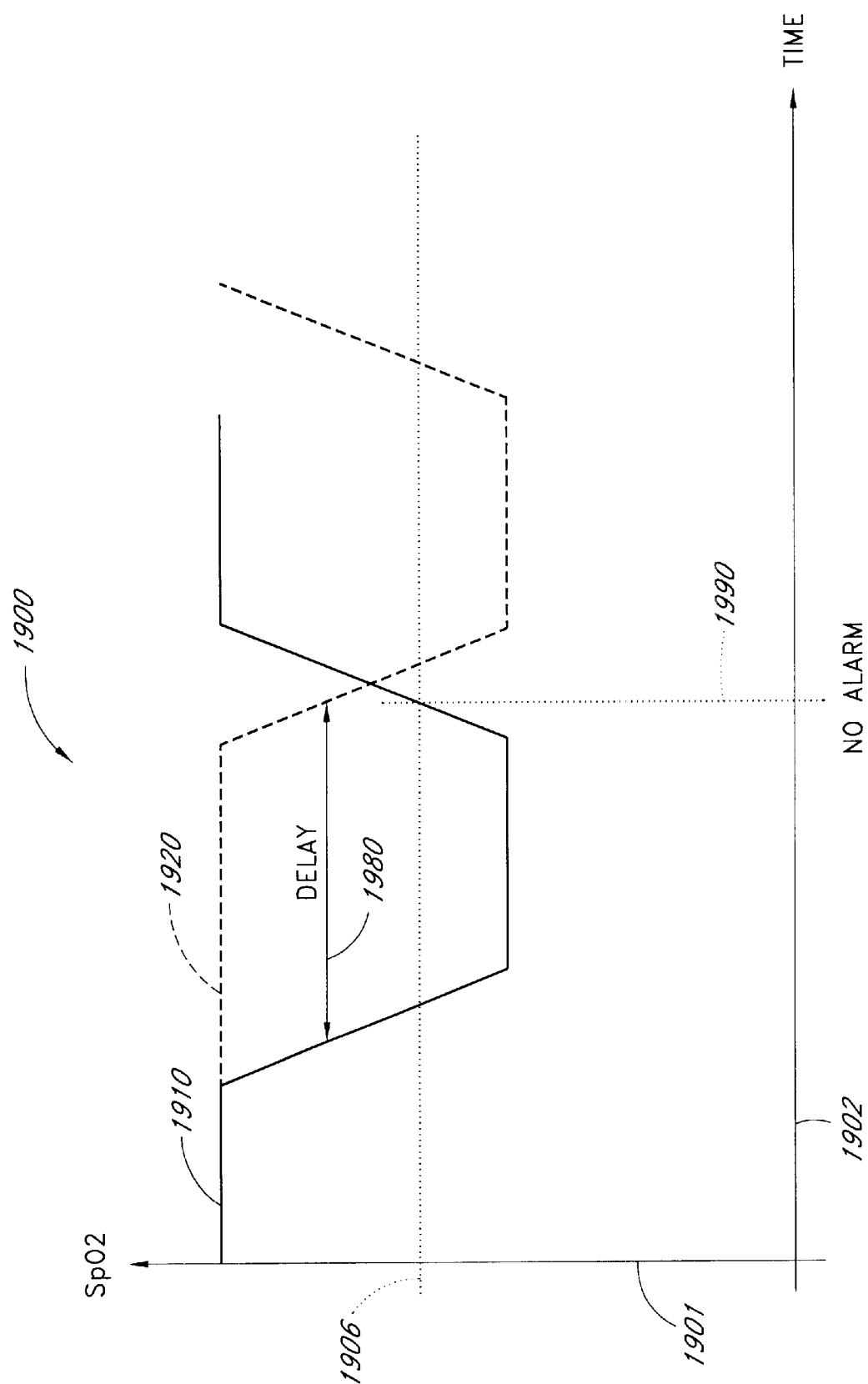

FIGS. 19A–D illustrate the operation of one embodiment of a confidence-based alarm according to the present invention. FIG. 19A illustrates an alarm with zero delay. FIGS. 19B–D illustrate an alarm with increasing amounts of delay. FIG. 19A is a chart 1900 having a vertical axis 1901 of saturation ($SpO_2$) and a horizontal axis 1902 of time. An alarm threshold 1906 is shown along the vertical axis 1901, corresponding to the alarm threshold input 1730 (FIG. 17). Depicted is saturation data 1910 corresponding to the PD 1710 (FIG. 17). An alarm is immediately triggered when saturation data 1910 falls below the alarm threshold 1906, and the duration of the alarm is the period of time the saturation data is below the threshold 1906.

FIG. 19B is an identical chart 1900 as described above, but depicting delayed saturation data 1920 corresponding to DPD 1832 (FIG. 18) that is time-shifted from the saturation data 1910 by a short delay 1940. In this example, both the saturation 1910 and the delayed saturation 1920 are below the alarm threshold 1906 during a time period 1950. During this time period 1950, the alarm trigger 1740 (FIG. 17) is asserted to generate an audio and/or visual warning that a desaturation event is occurring. The onset of the alarm is delayed 1940, as compared with FIG. 19A. The alarm functions similarly to a low pass filter that smoothes the saturation data 1910, preventing desaturation events that are less than the delay 1940 from triggering an alarm, as described with respect to FIG. 19D, below.

FIG. 19C is an identical chart 1900 as described above, but with the delayed saturation data 1920 time-shifted from the saturation data 1910 by a medium delay 1960. In this example, during the entire time period 1970 when the saturation data 1910 is below the alarm threshold 1906, the delayed saturation data 1920 is also below the threshold 1906. Thus, the alarm trigger 1740 (FIG. 17) would be asserted and a warning would be generated.

FIG. 19D is an identical chart 1900 as described above, but with the delayed saturation data 1920 time-shifted from the saturation data 1910 by a long delay 1980. In this example, at the time point 1990 when the saturation 1910 rises above the alarm threshold 1906, the delayed saturation 1920 has yet to fall below the threshold 1906. Thus, the alarm trigger 1740 (FIG. 17) would not be asserted and no warning would be generated. FIGS. 19A–D illustrate that the effect of an increasing data buffer delay is to increasingly delay the onset of the alarm trigger 1740 (FIG. 17) and to increasingly filter-out or smooth a relatively short drop in saturation 1910, which may be a false alarm during low signal quality conditions. Although the confidence-based alarm 1700 (FIG. 17) is described above in terms of an alarm delay to reduce false alarms, where the delay is a function of signal quality, one of ordinary skill in the art will recognize that the scope of present invention encompasses other mechanisms for reducing false alarms that are a function of physiological data confidence.

A pulse oximetry data confidence indicator has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. A data confidence indicator comprising:
   a plurality of physiological data and a plurality of signal quality measures derived from a physiological sensor output;
   a plurality of comparator outputs each responsive to one of said measures and a corresponding one of a plurality of thresholds;
   an alert trigger output combining said comparator outputs; and
   a low signal quality warning generated in response to said alert trigger output, said thresholds set so that said warning occurs during a time period when there is low confidence in said data.

2. The indicator of claim 1 wherein said warning is a display message that supplements a visual pulse indicator, said display message specifying low signal quality when said visual pulse indicator has an amplitude less than one-third full-scale.

3. The indicator of claim 1 wherein said signal quality measures comprise at least one of an integrity measure, a pulse rate density measure and a harmonic ratio measure.

4. The indicator of claim 3 wherein said thresholds comprise an integrity value of less than 0.3, a pulse rate density value of less than 0.7 and a harmonic ratio value of less than 0.8.

5. The indicator of claim 1 further comprising:
   a smoothing filter for said data;
   an adjustment for said smoothing filter that is a function of at least one of said signal quality measures;
   a predetermined alarm threshold for said data; and
   an alarm trigger responsive to said smoothing filter and said alarm threshold.

6. The indicator of claim 5 wherein said filter comprises:
   a buffer having said data as an input and a delay output, wherein the delay output comprises said data time-shifted according to said adjustment;
   a first comparator output responsive to said data and said threshold; and
   a second comparator output responsive to said delay output and said threshold, said comparator outputs combined so as to provide said alarm trigger.

7. A data confidence indicator comprising:
   a processor configured to derive a time-dependent physiological data set and a plurality of time-dependent signal quality measures from a physiological signal;
   a buffer configured to time-shift said data set by a delay to generate a delayed data set, said delay being a function of at least one of said signal quality measures;
   a threshold setting a limit for said data set and said delayed data set; and
   a warning generated when the levels of said data set and said delayed data set are beyond said threshold.

8. The data confidence indicator according to claim 7 further comprising:
   a first comparator output responsive to said data set and said threshold;
   a second comparator output responsive to said delayed data set and said threshold; and
   a combination of said comparator outputs providing an alarm trigger for said warning.

9. The data confidence indicator according to claim 8 further comprising a combination of said signal quality measures providing an alert trigger to generate a warning when confidence in said data set is low.

10. A data confidence indication method comprising the steps of:
  acquiring a signal from a physiological sensor;
  calculating a physiological data set from said signal;
  calculating a plurality of signal Quality measures from said signal;
  indicating on a display a level of confidence in said data set based upon at least one of said signal quality measures;
  utilizing said signal Quality measures to detect a low signal Quality period during which time said data set may be compromised;
  writing an alert message on said display during at least a portion of said low signal quality period;
  comparing each of said signal quality measures to a corresponding one of a plurality of thresholds to generate a plurality of trigger inputs; and
  combining said trigger inputs to trigger a low signal quality warning.

11. A data confidence indication method comprising the steps of:
  acquiring a signal from a physiological sensor:
  calculating a physiological data set from said signal;
  calculating a plurality of signal quality measures from said signal;
  indicating on a display a level of confidence in said data set based upon at least one of said signal quality measures;
  setting an alarm limit for said data set;
  filtering said data set to generate an alarm trigger based upon said alarm limit; and;
  adjusting characteristics of said filtering step according to said signal quality measures so that more filtering is applied during said low signal quality period.

12. The data confidence indication method according to claim 11 wherein said filtering step comprises the substeps of:
  time-shifting said data set to create a delayed data set;
  comparing said data set to a threshold to generate a first trigger input;
  comparing said delayed data set to said threshold to generate a second trigger input; and
  combining said trigger inputs to generate said alarm trigger.

13. The data confidence indication method according to claim 12 wherein said adjusting comprises the substep of changing the amount of said time-shifting according to said signal quality measures.

14. A data confidence indication method comprising the steps of:
  acquiring a signal from a physiological sensor;
  calculating a physiological data set from said signal;
  calculating a plurality of signal quality measures from said signal;
  setting an alarm threshold for said data set; and
  delaying an alarm trigger when said data set exceeds said threshold as a function of at least one of said signal Quality measures so as to reduce the probability of false alarms, wherein delaying the alarm trigger comprises:
    time-shifting said data set by a delay to generate a delayed data set, wherein said delay is a function of at least one of said signal quality measures;
    comparing said data set to said threshold to create a first limit output;
    comparing said delayed data set to said threshold to create a second limit output; and
    combining said limit outputs to generate said alarm trigger.

15. A data confidence indication method comprising the steps of:
  acquiring a signal from a physiological sensor;
  calculating a physiological data set from said signal;
  calculating a plurality of signal quality measures from said signal;
  setting an alarm threshold for said data set;
  delaying an alarm trigger when said data set exceeds said threshold as a function of at least one of said signal quality measures so as to reduce the probability of false alarms;
  comparing each of said signal quality measures to a corresponding one of a plurality of thresholds to generate a plurality of trigger inputs; and
  combining said trigger inputs to trigger a low signal quality warning.

* * * * *

UNITED STATES PATENT AND TRADEMARK OFFICE
CERTIFICATE OF CORRECTION

PATENT NO. : 6,684,090 B2
APPLICATION NO. : 09/858114
DATED : January 27, 2004
INVENTOR(S) : Ammar Al Ali et al.

It is certified that error appears in the above-identified patent and that said Letters Patent is hereby corrected as shown below:

In Drawing Sheet 9, Box 710, Fig. 7, please delete "C1 C2" and insert -- $C_1$ $C_2$ --, therefore.

In Drawing Sheet 9, Box 720, Fig. 7, please delete "C1 C2" and insert -- $C_1$ $C_2$ --, therefore.

In Drawing Sheet 21, Fig. 19A, please delete "SpO2" and insert -- $SpO_2$ --, therefore.

In Drawing Sheet 22, Fig. 19B, please delete "SpO2" and insert -- $SpO_2$ --, therefore.

In Drawing Sheet 23, Fig. 19C, please delete "SpO2" and insert -- $SpO_2$ --, therefore.

In Drawing Sheet 24, Fig. 19D, please delete "SpO2" and insert -- $SpO_2$ --, therefore.

Signed and Sealed this

Twenty-sixth Day of June, 2007

JON W. DUDAS
*Director of the United States Patent and Trademark Office*

UNITED STATES PATENT AND TRADEMARK OFFICE
CERTIFICATE OF CORRECTION

PATENT NO. : 6,684,090 B2  
APPLICATION NO. : 09/858114  
DATED : January 27, 2004  
INVENTOR(S) : Ammar Al Ali et al.

It is certified that error appears in the above-identified patent and that said Letters Patent is hereby corrected as shown below:

Drawing, In Sheet 9, Box 710, Fig. 7, please delete "C1 C2" and insert -- $C_1$ $C_2$ --, therefore.

Drawing, In Sheet 9, Box 720, Fig. 7, please delete "C1 C2" and insert -- $C_1$ $C_2$ --, therefore.

Drawing, In Sheet 21, Fig. 19A, please delete "SpO2" and insert -- $SpO_2$ --, therefore.

Drawing, In Sheet 22, Fig. 19B, please delete "SpO2" and insert -- $SpO_2$ --, therefore.

Drawing, In Sheet 23, Fig. 19C, please delete "SpO2" and insert -- $SpO_2$ --, therefore.

Drawing, In Sheet 24, Fig. 19D, please delete "SpO2" and insert -- $SpO_2$ --, therefore.

At column 2, line 1-24, delete "An intelligent, rule-based processor provides……………….when data confidence is very low." and insert -- A data confidence indicator includes a plurality of physiological data and a plurality of signal quality measures derived from a physiological sensor output, and a plurality of comparator outputs each responsive to one of the measures and a corresponding one of a plurality of thresholds. An alert triggers outputs combines the comparator outputs. A low signal quality warning is generated in response to the alert trigger output, wherein the thresholds are set so that the warning occurs during a time period when there is low confidence in the data. --, therefore.

UNITED STATES PATENT AND TRADEMARK OFFICE
CERTIFICATE OF CORRECTION

PATENT NO. : 6,684,090 B2
APPLICATION NO. : 09/858114
DATED : January 27, 2004
INVENTOR(S) : Ammar Al Ali et al.

It is certified that error appears in the above-identified patent and that said Letters Patent is hereby corrected as shown below:

At column 17, line 5, In claim 10, delete "Quality" and insert -- quality --, therefore.

At column 17, line 10 (Approx.), In claim 10, delete "Quality" and insert --quality --, therefore.

At column 17, line 11 (Approx.), In claim 10, delete "Quality" and insert --quality --, therefore.

At column 17, line 24, In claim 11, after "sensor" delete ":" and insert -- ; --, therefore.

At column 17, line 34, In claim 11, after "and" delete ";".

At column 18, line 16, In claim 14, delete "Quality" and insert -- quality --, therefore.

Signed and Sealed this

Thirteenth Day of May, 2008

JON W. DUDAS
*Director of the United States Patent and Trademark Office*

(12) EX PARTE REEXAMINATION CERTIFICATE (9981st)
United States Patent
Ali et al.

(10) Number: US 6,684,090 C1
(45) Certificate Issued: Dec. 12, 2013

(54) PULSE OXIMETRY DATA CONFIDENCE INDICATOR

(75) Inventors: Ammar Al Ali, Tustin, CA (US); Divya S. Breed, Laguna Niguel, CA (US); Jerome J. Novak, Aliso Viejo, CA (US); Massi E. Kiani, Laguna Niguel, CA (US)

(73) Assignee: Masimo Corporation, Irvine, CA (US)

Reexamination Request:
No. 90/012,567, Sep. 14, 2012

Reexamination Certificate for:
Patent No.: 6,684,090
Issued: Jan. 27, 2004
Appl. No.: 09/858,114
Filed: May 15, 2001

Certificate of Correction issued Jun. 26, 2007
Certificate of Correction issued May 13, 2008

Related U.S. Application Data

(63) Continuation-in-part of application No. 09/478,230, filed on Jan. 6, 2000, now Pat. No. 6,606,511.

(60) Provisional application No. 60/115,289, filed on Jan. 7, 1999.

(51) Int. Cl.
*A61B 5/00* (2006.01)
*A61B 5/024* (2006.01)

(52) U.S. Cl.
USPC .......................... 600/323; 600/324; 600/336

(58) Field of Classification Search
None
See application file for complete search history.

(56) References Cited

To view the complete listing of prior art documents cited during the proceeding for Reexamination Control Number 90/012,567, please refer to the USPTO's public Patent Application Information Retrieval (PAIR) system under the Display References tab.

*Primary Examiner* — Anjan K. Deb

(57) ABSTRACT

An intelligent, rule-based processor provides a pulse indicator designating the occurrence of each pulse in a pulse oximeter-derived photo-plethysmograph waveform. When there is relatively no distortion corrupting the plethysmograph signal, the processor analyzes the shape of the pulses in the waveform to determine where in the waveform to generate the pulse indication. When distortion is present, looser waveform criteria are used to determine if pulses are present. If pulses are present, the pulse indication is based upon an averaged pulse rate. If no pulses are present, no indication occurs. The pulse indicator provides a trigger and amplitude output. The trigger output is used to initiate an audible tone "beep" or a visual pulse indication on a display, such as a vertical spike on a horizontal trace or a corresponding indication on a bar display. The amplitude output is used to indicate data integrity and corresponding confidence in the computed values of saturation and pulse rate. The amplitude output can vary a characteristic of the pulse indicator, such as beep volume or frequency or the height of the visual display spike.

The visual pulse indicator is supplemented by a signal quality alert. Combined with several indicators of signal quality, the alert is used to initiate a warning when data confidence is very low. The alert may be in the form of a message generated on the pulse oximeter display to warn that the accuracy of saturation and pulse rate measurements may be compromised. A confidence-based alarm utilizes signal quality measures to reduce the probability of false alarms when data confidence is low and to reduce the probability of missed events when data confidence is high.

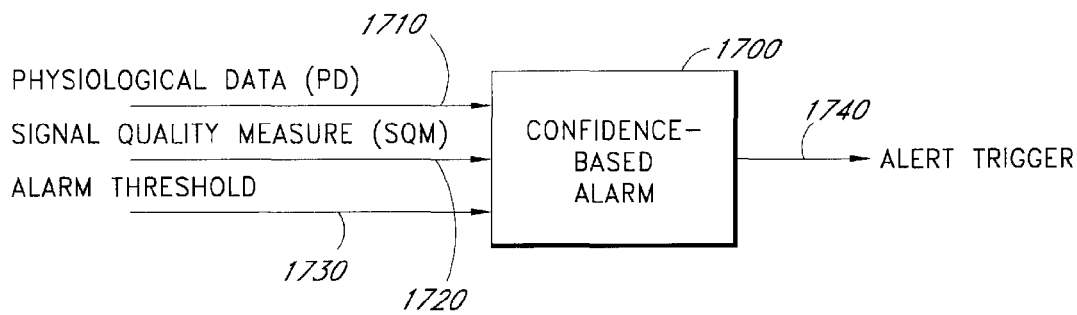

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 11 is confirmed.

Claim 1 is cancelled.

Claim 10 is determined to be patentable as amended.

Claims 2-9 and 12-15 were not reexamined.

10. A data confidence indication method comprising the steps of:

acquiring a signal from a physiological sensor;

calculating a physiological data set from said signal;

calculating a plurality of signal quality measures from said signal;

*filtering said physiological data set as a function of said plurality of signal quality measures, wherein said filtering is increased as said signal quality measures indicate worsening signal quality; and* indicating on a display a level of confidence in said data set based upon at least one of said signal quality measures;

*wherein said indicating step comprises the substeps of:* utilizing said signal quality measures to detect a low signal quality period during which time said data set may be compromised; *and* writing an alert message on said display during at least a portion of said low signal quality period; *and*

*wherein said utilizing step comprises the further substeps of:* comparing each of said signal quality measures to a corresponding one of a plurality of thresholds to generate a plurality of trigger inputs; and combining said trigger inputs to trigger a low signal quality warning.

* * * * *